(12) United States Patent
Mairhofer et al.

(10) Patent No.: US 11,046,963 B2
(45) Date of Patent: Jun. 29, 2021

(54) UNCOUPLING GROWTH AND PROTEIN PRODUCTION

(71) Applicant: enGenes Biotech GmbH, Vienna (AT)

(72) Inventors: Juergen Mairhofer, Vienna (AT); Gerald Striedner, Vienna (AT); Reingard Grabherr, Vienna (AT); Monika Wilde, Vienna (AT)

(73) Assignee: enGenes Biotech GmbH, Vienna (AT)

( * ) Notice: Subject to any disclaimer, the term of this patent is extended or adjusted under 35 U.S.C. 154(b) by 0 days.

(21) Appl. No.: 15/569,024

(22) PCT Filed: Apr. 29, 2016

(86) PCT No.: PCT/EP2016/059597
§ 371 (c)(1),
(2) Date: Oct. 24, 2017

(87) PCT Pub. No.: WO2016/174195
PCT Pub. Date: Nov. 3, 2016

(65) Prior Publication Data
US 2018/0282737 A1    Oct. 4, 2018

(30) Foreign Application Priority Data

Apr. 30, 2015  (LU) .......................................... 92705
Oct. 16, 2015  (EP) ..................................... 15190078

(51) Int. Cl.
| | | |
|---|---|---|
| C12N 5/00 | (2006.01) | |
| C12N 15/73 | (2006.01) | |
| C07K 14/005 | (2006.01) | |
| C12N 9/12 | (2006.01) | |

(52) U.S. Cl.
CPC ............ *C12N 15/73* (2013.01); *C07K 14/005* (2013.01); *C12N 9/1247* (2013.01); *C12N 2740/16322* (2013.01); *C12N 2795/00022* (2013.01); *C12N 2795/10222* (2013.01)

(58) Field of Classification Search
CPC .................. C12N 15/73; C12N 9/1247; C12N 2740/16322; C12N 2795/00022; C12N 2795/10222; C07K 14/005
See application file for complete search history.

(56) References Cited

U.S. PATENT DOCUMENTS

| | | | | |
|---|---|---|---|---|
| 2005/0032086 A1* | 2/2005 | Sakanyan | ............ | C12N 9/1247 435/6.13 |
| 2008/0299617 A1* | 12/2008 | Fang | ...................... | C12N 15/67 435/69.6 |
| 2018/0087045 A1* | 3/2018 | Blake | ...................... | C12Q 1/68 |

FOREIGN PATENT DOCUMENTS

| | | |
|---|---|---|
| EP | 0 178 863 | 4/1986 |
| JP | S61100197 A | 5/1986 |
| WO | WO 88/10307 | 12/1988 |
| WO | WO 91/05866 | 5/1991 |
| WO | WO 97/34996 | 9/1997 |
| WO | WO 97/41243 | 11/1997 |
| WO | WO 2007/071959 | 6/2007 |
| WO | WO 2015/036622 | 3/2015 |

OTHER PUBLICATIONS

Savalia et al., Role of the T7 gp2 inhibitor of host RNA polymerase in phage development; JMB, vol. 402, pp. 118-126, 2010 (Year: 2010).*
Studier, Science, 176, 367-376, (Year: 1972).*
Cámara, Beatriz, et al.: "T7 phage protein Gp2 inhibits the *Escherichia coli* RNA polymerase by antagonizing stable DNA strand separation near the transcription start site," PNAS, Feb. 2, 2010, vol. 107(5), pp. 2247-2252.
Hesselbach, Bruce A., et al.: "'Host Shutoff' Function of Bacteriophage T7: Involvement of T7 Gene 2 and Gene 0.7 in the Inactivation of *Escherichia coli* RNA Polymerase," Journal of Virology, Dec. 1977, pp. 736-745.
Mukherjee, K. J., et al.: "Studies of Single-Chain Antibody Expression in Quiescent *Escherichia coli*," Applied and Environmental Microbiology, vol. 70(5), pp. 3005-3012, May 2004.
Rowe, Duncan C.D., et al.: "The Quiescent-Cell Expression System for Protein Synthesis in *Escherichia coli*," Applied and Environmental Microbiology, vol. 65(6), pp. 2710-2715, Jun. 1999.
Schweiger, Manfred, et al.: "Negative Control of Protein Synthesis after Infection with Bacteriophage T7," PNAS, vol. 69(8), pp. 2203-2207. Aug. 1972.
Sheppard, Carol, et al.: "Reprint of: Inhibition of *Escherichia coli* RNAp by T7 Gp2 protein: Role of Negatively Charged Strip of Amino Acid Residues in Gp2," Journal of Molecular Biology, 2011, 412, pp. 832-841.
Studier, F. William, et al.: "Use of Bacteriophage T7 RNA Polymerase to Direct Selective High-level Expression of Cloned Genes," Journal of Molecular Biology, 1986, 189, pp. 113-130.
Tabor, Stanley, et al.: "A bacteriophage T7 RNA polymerase/promoter system for controlled exclusive expression of specific genes," PNAS, USA, vol. 82, pp. 1074-1078, Feb. 1985.
Watnick, Randolph S., et al.: "The carboxyl terminus of phage HK022 Nun includes a novel zinc-binding motif and a tryptophan required for transcription termination," Genes and Development, 14: 731-739, 2000.

(Continued)

*Primary Examiner* — Catherine S Hibbert
(74) *Attorney, Agent, or Firm* — Cooley LLP

(57) ABSTRACT

The present invention is in the field of recombinant biotechnology, in particular in the field of protein expression. The invention generally relates to methods of increasing the expression level of a protein of interest of a bacterial host cell in a production process. The invention relates particularly to improving the capacity of a bacterial host cell to express a protein of interest by expressing a phage protein during the production process which inhibits growth of the bacterial host cell. Decoupling growth of the bacterial host cell of manufacturing of the protein of interest during the production process reduces (i) the metabolic burden, (ii) oxygen demand, (iii) metabolic heat development, and (iv) avoids stress response caused by heterologous protein expression and thereby increases the capacity of a host cell to produce the protein of interest. The present invention also relates to uses of the host cell for protein expression, cell culture technology, and more specifically to culturing host cells to produce a protein of interest.

14 Claims, 21 Drawing Sheets

Figure 1:
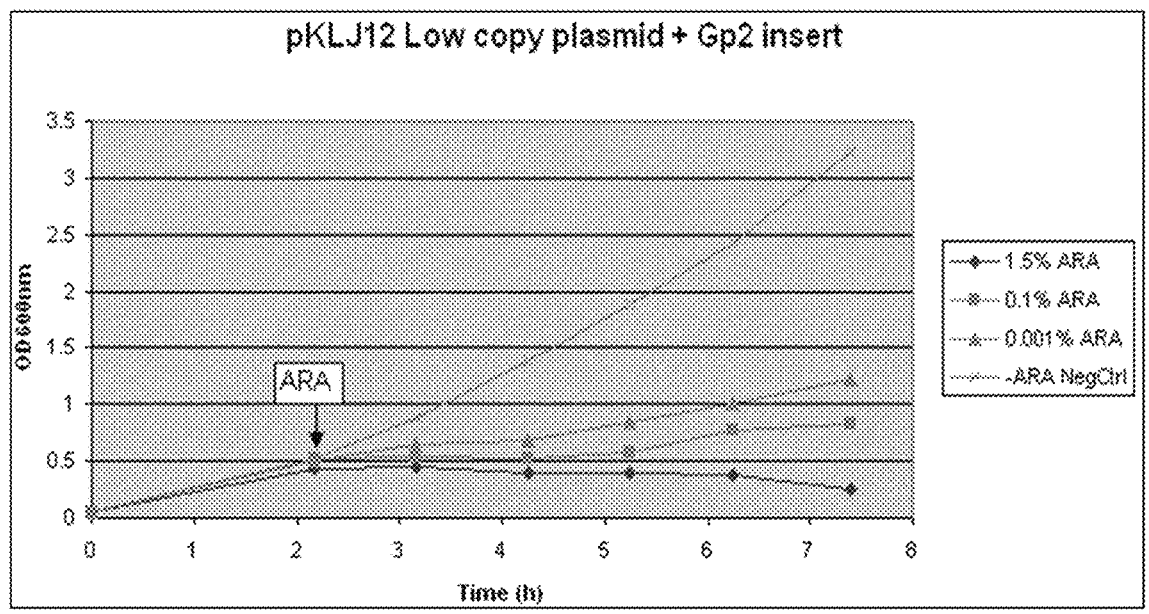

Specification includes a Sequence Listing.

(56) References Cited

OTHER PUBLICATIONS

International Search Report issued in International patent application No. PCT/EP2016/059597, dated Jul. 28, 2016.
Shadrin, et al. Substitutions in the *Escherichia coli* RNA Polymerase Inhibitor T7 GPS That Allow Inhibition of Transcription When the Primary Interaction Interfaces Between G2 and RNA Polymerase Becomes Compromised, Microbiology, 2012, vol. 158, p. 2753-2764.
Japanese Office Action dated Apr. 7, 2020 issued in Application No. JP2018-507775.
Li, Xiaokun et al. Preparation Principles and Applications of Genetic Engineering Drugs. Jina University Press, p. 38. Aug. 31, 2008.
Chinese Office Action dated Sep. 10, 2020.

\* cited by examiner

Figure 3
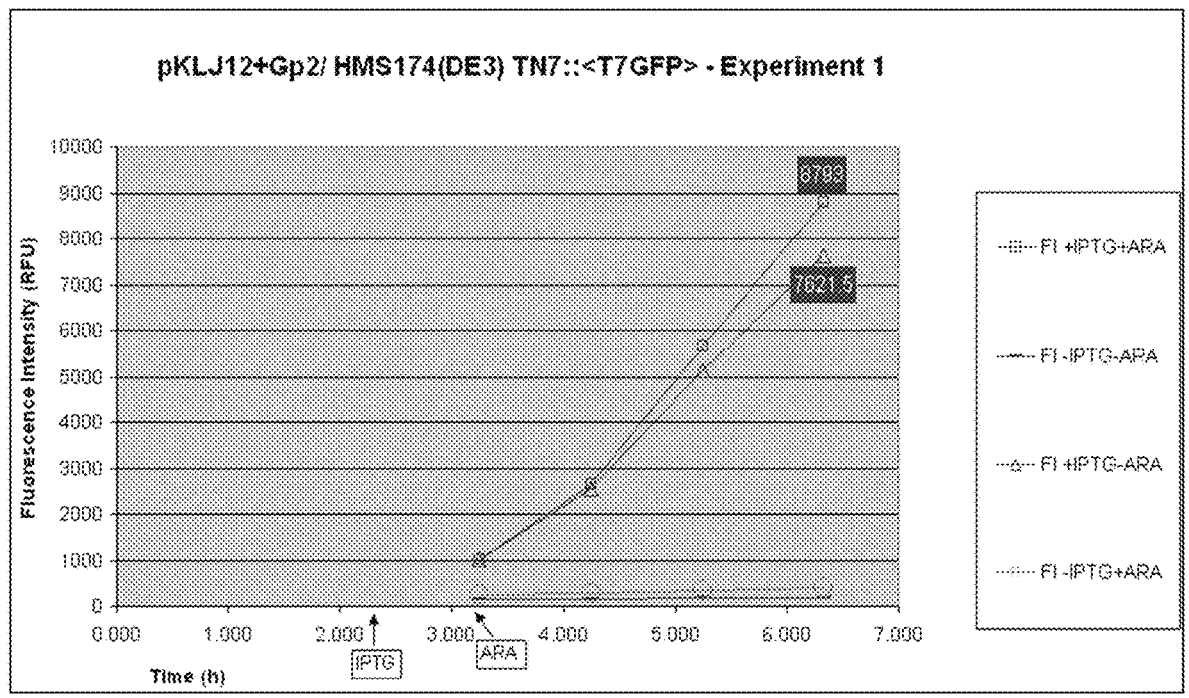
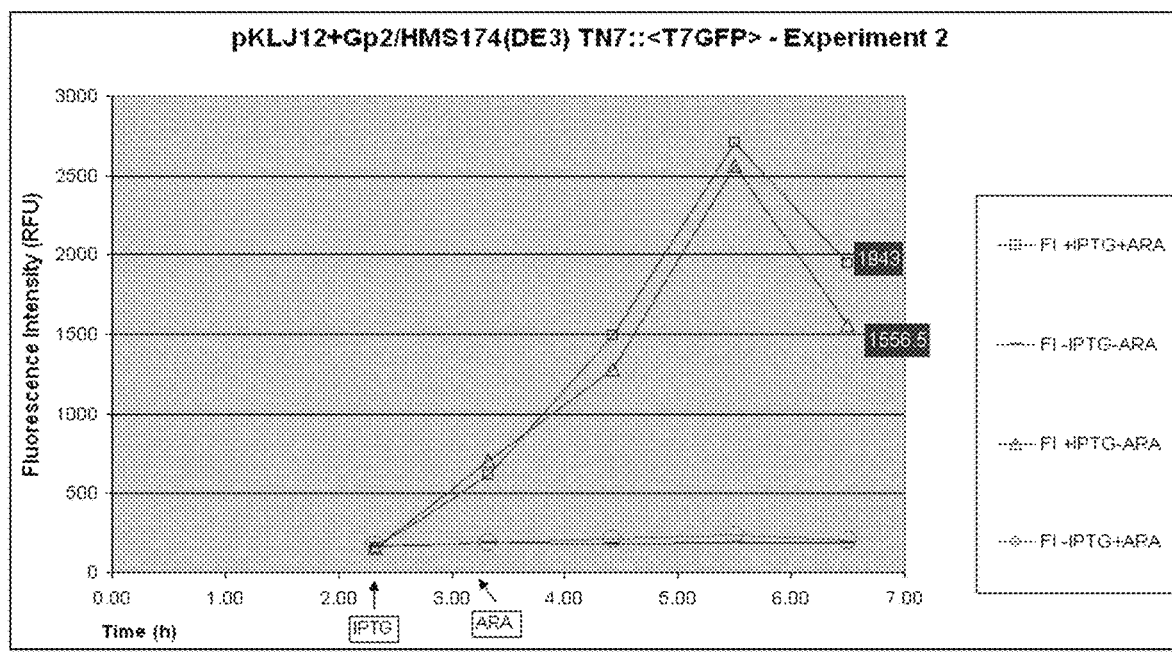

Figure 3 (con t'd)
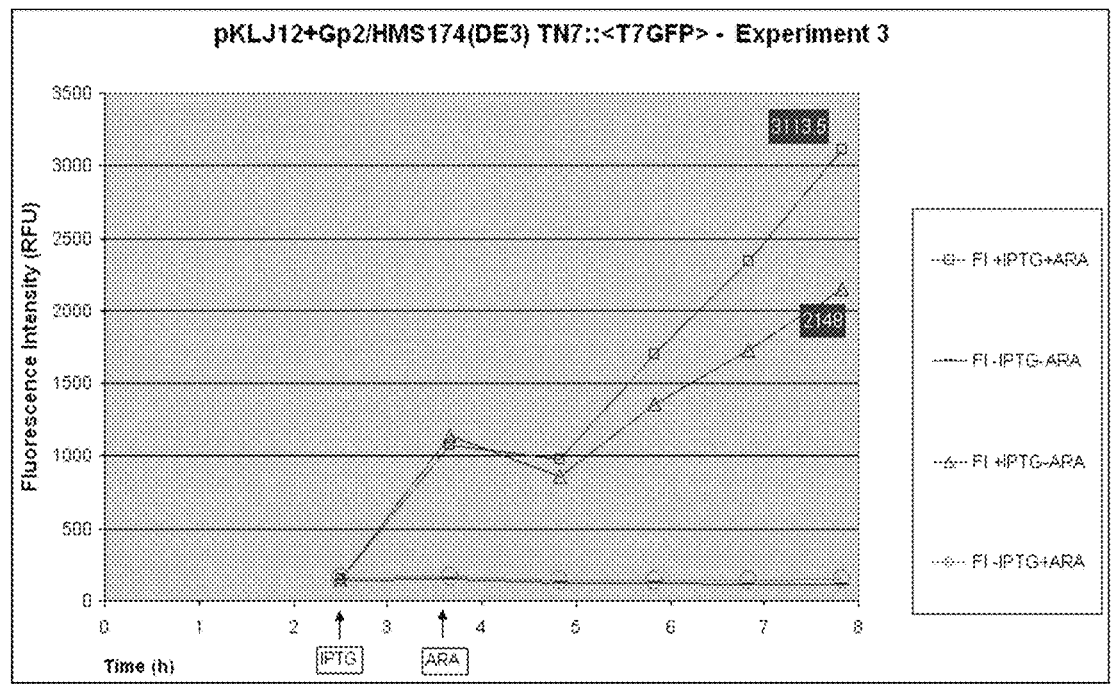
Figure 4
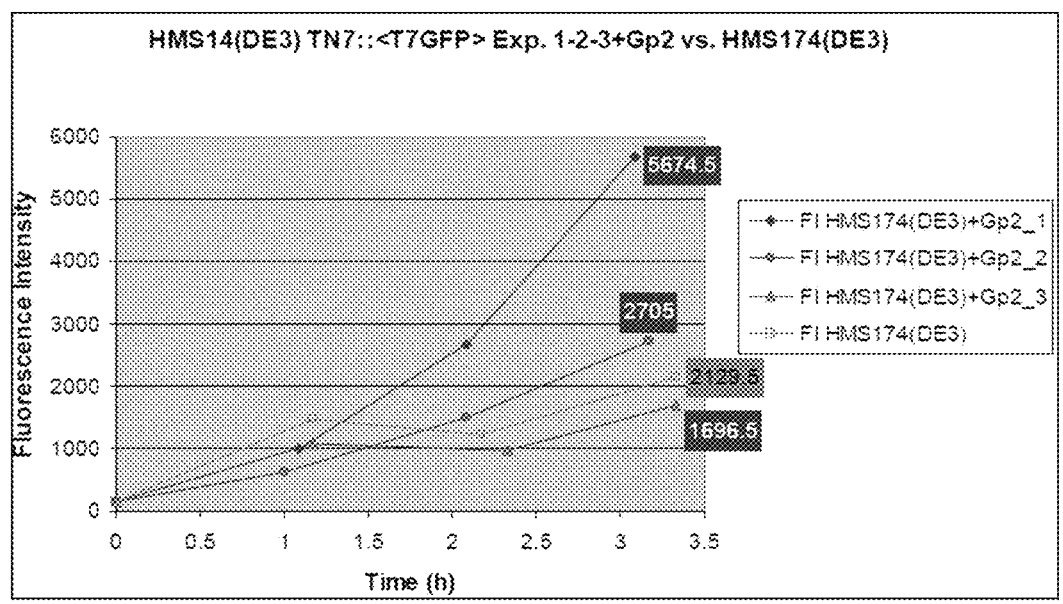

Figure 5

SEQ ID NO: 1 (Gp2)

MSNVNTGSLSVDNKKFWATVESSEHSFEVPIYAETLDEALELAEWQYVPAGFEVTRVRPCVAPK

SEQ ID NO: 2 (Nun)

MVKKTIYVNPDSGQNRKVSDRGLTSRDRRRIARWEKRIAYALKNGVTPGFNAIDDGPEYKINEDPMDKVDKALATPFPRDVEKIEDEKYEDVMHRVVNHAHQRNPNKKWS

SEQ ID NO: 3 (Gp0.7)

MNTINIAKNDFSDIELAAIPFNTLADHYGERLAREQLALEHESYEMGEARFRKMFERQLKAGEV
ADNAAAKPLITTLLPKMIARINDWFEEVKAKRGKRPTAFQFLQEIKPEAVAYITIKTTLACLTSAD
NTTVQAVASAIGRAIEDEARFGRIRDLEAKHFKKNVEEQLNKRVGHVYKKAFMQVVEADMLSK
GLLGGEAWSSWHKEDSIHVGVRCIEMLIESTGMVSLHRQNAGVVGQDSETIELAPEYAEAIAT
RAGALAGISPMFQPCVVPPKPWTGITGGGYWANGRRPLALVRTHSKKALMRYEDVYMPEVY
KAINIAQNTAWKINKKVLAVANVITKWKHCPVEDIPAIEREELPMKPEDIDMNPEALTAWKRAAA
AVYRKDKARKSRRISLEFMLEQANKFANHKAIWFPYNMDWRGRVYAVSMFNPQGNDMTKGL
LTLAKGKPIGKEGYYWLKIHGANCAGVDKVPFPERIKFIEENHENIMACAKSPLENTWWAEQD
SPFCFLAFCFEYAGVQHHGLSYNCSLPLAFDGSCSGIQHFSAMLRDEVGGRAVNLLPSETVQ
DIYGIVAKKVNEILQADAINGTDNEVVTVTDENTGEISEKVKLGTKALAGQWLAYGVTRSVTKRS
VMTLAYGSKEFGFRQQVLEDTIQPAIDSGKGLMFTQPNQAAGYMAKLIWESVSVTVVAAVEAM
NWLKSAAKLLAAEVKDKKTGEILRKRCAVHWVTPDGFPVWQEYKKPIQTRLNLMFLGQFRLQ
PTINTNKDSEIDAHKQESGIAPNFVHSQDGSHLRKTVVWAHEKYGIESFALIHDSFGTIPADAAN
LFKAVRETMVDTYESCDVLADFYDQFADQLHESQLDKMPALPAKGNLNLRDILESDFAFA

SEQ ID NO: 4 (Gp6)

MRKSLIMGTKEDVAKMKAKRQMNKAVTFAERYSTSEPVRRIVTFNHPAIKGM

SEQ ID NO: 5 (Gp8)

MEQLNYGYKIKRNQVRGSWLFLVYGKPIYELHRGEKSKTYYVTHIATGKTPACAGLLRDAIMKA
CMLEGLL

**SEQ ID NO: 6 (A*)**

MKSRRGFAIQRLMNAMRQAHADGWFIVFDTLTLADDRLEAFYDNPNALRDYFRDIGRMVLAA
EGRKANDSHADCYQYFCVPEYGTANGRLHFHAVHFMRTLPTGSVDPNFGRRVRNRRQLNSL
QNTWPYGYSMPIAVRYTQDAFSRSGWLWPVDAKGEPLKATSYMAVGFYVAKYVNKKSDMDL
AAKGLGAKEWNNSLKTKLSLLPKKLFRIRMSRNFGMKMLTMTNLSTECLIQLTKLGYDATPFN
QILKQNAKREMRLRLGKVTVADVLAAQPVTTNLLKFMRASIKMIGVSNLQSFIASMTQKLTLSDI
SDESKNYLDKAGITTACLRIKSKWTAGGK

Figure 5 (cont'd)

SEQ ID NO: 7 (YkzG, Epsilon-Subunit)

MIYKVFYQEKADEVPVREKTDSLYIEGVSERDVRTKLKEKKFNIEFITPVDGAFLEYEQQSENFKVLEL

SEQ ID NO: 8 (Bacillus phage SPO1 GP40)

MHIYTYWGLKYVPSNSTMVAKEGDLILLGNEVHKVVKVLHRFRNITDLQITNWKGTETRYNLHVTEYKVL
VPYDTHKEENEAMSDSLITHNGKDYVLCKIPARVGDLIRTEDKRVWEVLQKSKDGLVLYNEEKGEQRSAV
YSEIGPYHVLVPRDTDTHTPTREELAAVIMNKAFTRTETQDSQEDTGTHKGLGLTGTDLYHSLRDLDAKV
QSGYYTATENEEDVKSEIEATKKHMKAVKESGKTVNDYRKEENTKRCKLKALTNKFNRLFLKSVIDTDSL
QVGKAYLIGGRDMKNVHGLYTGTTFDQQHANFLIVETDRMHRTLTVSAEQLFAEERHIVDIEKRVEQTED

SEQ ID NO: 9 (Staphylococcus phage G1 GP67)

MTNSKKKGDTFERKIAKELTAWWGYQFNRSPQSGGASWGKDNNAVGDIVVPQEANFPLVVECKHREEWTIDNVLLNN
REPHTWWEQVINDSSKVNKTPCLIFTRNRAQSYVALPYDEKVYEDLRNNEYPVMRTDFIIDNIRKDKFFYDVLITTM
NGLTSFTPSYIISCYDKKDIKPYKKVESNLSEVSKHEDELINDLLSDI

SEQ ID NO: 10 (Thermus thermophilus phage P23-45 GP39)

MVEGFVEPYIRLFEAIPDAETELATFYDADLDTLPPRMFLPSGDLYTPPGPVRLEEIKRKRRVRLVKVSIYRFEHVG
LGLAARPYAYAYAWQGDNGILHLYHAPVVLEDVPEVLELDEVTYNESYVRLMRAMGHVDAFIDL

SEQ ID NO: 11 (Enterobacteria phage PhiEco32 GP79)

MDMFSLEDLVQNGMMEQKEPLIVGSRKELRKLCEEWGITNQRMIGNQFSAIVTFLKRGDKYSMECVERIITEAQQDK
GVTYL

SEQ ID NO: 12 (Xanthomonas oryzae bacteriophage Xp10 P7)

MNEFTQISGYVNAFGSQRGSVLTVKVENDEGWTLVEEDFDRADYGSDPEFVAEVSSYLKRNGGIKDLTKVLTR

SEQ ID NO: 13 (Enterobacteria phage T4 Alc)

MDLQLITTEMVVEAYGDTTDGISVFKGNRRVGYITGLKKDLAKQVKRKTTIKEYRNRRLEQARDMLPDAVEEMKVFL
ENQLAKYDCEVFINQTQPNVHINSCKCYIIVNPLTGKHRLGISNPNRSASDMAEDVEACFKISKSPAEHHILINGLS
QDDIVEVIKTLCM

SEQ ID NO: 14 (Enterobacteria phage T4 Asia)

MNKNIDTVREIITVASILIKFSREDIVENRANFIAFLNEIGVTHEGRKLNQNSFRKIVSELTQEDKKTLIDEFNEGF
EGVYRYLEMYTNK

Figure 8

| | Growth decoupled system | | standard system |
|---|---|---|---|
| | S    IB | S    IB | S    IB |
| GFP | | | |
| Lysozyme | | | |
| hours induced | 4 h | 14 h | 7h |
| GFP in soluble Protein fraction | 25 % | 63% | 28% |

Figure 14 (cont'd)

| well | raw vol. | BSA/HIV1-P [µg/ml] |
|---|---|---|
| 2 | 1.50E+08 | 146.4 |
| 3 | 7.52E+07 | 79 |
| 4 | 7.89E+06 | 19 |
| 5 | 0.00E+00 | 0 |
| 6 | 0.00E+00 | 0 |
| 7 | 2.01E+07 | 29.5 |
| 8 | 5.40E+06 | 16.3 |
| 9 | 2.60E+07 | 34.8 |
| 10 | 3.68E+07 | 44.5 |
| 11 | 2.24E+07 | 31.6 |
| 12 | 3.08E+07 | 39.2 |
| 13 | 3.00E+07 | 34.3 |
| 14 | 7.49E+07 | 70.2 |
| 15 | 2.60E+07 | 31.1 |
| 16 | 1.16E+08 | 103.1 |
| 17 | 1.92E+07 | 25.6 |
| 18 | 7.75E+07 | 72.3 |
| 19 | 1.44E+07 | 21.8 |
| 20 | 1.07E+08 | 96.0 |

UNCOUPLING GROWTH AND PROTEIN PRODUCTION

CROSS REFERENCE TO RELATED APPLICATIONS

This application is a U.S. Nation Stage of PCT international Application Number PCT/EP2016/059597, which was filed on Apr. 29, 2016, which claims priority to Luxembourg Patent Application No. 92705, which was filed on Apr. 30, 2015, and European Patent Application No. 15190078.4, which was filed on Oct. 16, 2015 the disclosures of each of which is incorporated herein by reference in its entirety.

The present invention is in the field of recombinant biotechnology, in particular in the field of protein expression. The invention generally relates to methods of increasing the expression level of a protein of interest of a bacterial host cell in a production process. The invention relates particularly to improving the capacity of a bacterial host cell to express a protein of interest by expressing a phage protein during the production process which inhibits growth of the bacterial host cell. Decoupling growth of the bacterial host cell in the manufacture of the protein of interest during the production process reduces (i) the metabolic burden, (ii) oxygen demand, (iii) metabolic heat development, and (iv) avoids stress response caused by heterologous protein expression, thereby increasing the capacity of a host cell to produce the protein of interest. The present invention also relates to uses of the host cell for protein expression, cell culture technology, and also to culturing host cells to produce a protein of interest.

Successful production of proteins of interest (POI) has been accomplished both with many prokaryotic hosts. The most prominent examples are bacteria like *Escherichia coli*, *Bacillus subtilis*, *Pseudomonas fluorescens*, *Streptomyces griseus*, or *Corynebacterium glutamicum*. While the yield of some proteins is readily achieved at high rates, many other proteins are only produced at comparatively low levels.

A great number of biological pharmaceuticals (e.g. antibodies or functional fragments thereof) have been produced in the last decade and an increasing number is nearing approval for use in humans but their efficient production remains a challenging task. Therapeutically active doses are often in the order of milligram (mg) per administration. Thus, considerable amounts of protein are needed as active ingredients, making an efficient and cost-effective production worthwhile.

Bacterial cell expression systems have long been, and still are, one of the major tools for production of these types of molecules. The key objective of process optimization is to achieve a high yield of product having the required quality at the lowest possible cost, which is often determined by the properties of a specific expression construct or system. For example, high-level recombinant protein expression may overwhelm the metabolic capacity of a host cell and consequently leads to plasmid loss, reduced oxygen transfer, generation of toxic by-products, formation of inclusion bodies, and/or triggering of a stress response which often impairs efficient protein production. It is also known that sometimes high expression of an mRNA encoding a protein of interest does not necessarily lead to high amounts of the protein. Different approaches have been taken by scientists to deal with these problems.

For example, the expression of a recombinant protein can be further increased by optimizing the gene dosage encoding the protein of interest, by using a suitable promoter or by optimizing the codon usage of the gene encoding the protein of interest according to the employed host cell. Several other parameters have been shown to affect the expression level of a recombinant protein in a host cell, such as expression vector design, media composition, growth temperature, chaperone co-expression, mRNA stability, translation initiation and epigenetic processes.

However, high level of protein yield in host cells may be limited at one or more different steps, like folding, disulfide bond formation, glycosylation, transport within the cell, or release from the cell. Many of the mechanisms involved are still not fully understood and cannot be predicted on the basis of the current knowledge of the state-of-the-art, even when the DNA sequence of the entire genome of a host organism is available.

Another issue with the production of proteins in host cell is a potential toxicity of such proteins for the host cell. Accordingly, the concept of so-called quiescent (Q)-cells was developed (WO 2007/071959). In Q-cells normal cellular mechanisms can be shut down which allows production of toxic proteins. In order to shut down Q-cells indole has to be added. For some applications, however, indole may not be desirable. Another concept of shifting the production machinery of a host cell towards the production of a protein of interest only is the single protein production (SSP) system in *E. coli*. A so-called mRNA interferase is expressed which cleaves RNA at ACA nucleotide sequences, while the mRNA encoding the protein of interest is devoid of ACA base triplets (Suzuki et al. (2007), Nature Protocols 2(7), 1802.1810). A further option to direct the metabolic capacity of the host cell towards production of a recombinant protein rather than growth is to make use of RNA interference to cause a cell cycle arrest and to thus direct metabolic fluxes towards product formation (Ghosh et al. (2012), Microbial Cell Factories 11:93).

Given the various issues in the prior art with respect to the production of proteins in reasonable amount, also including potentially toxic proteins in host cells, despite many advantages that have been made throughout the past years, there is still a need for identifying and developing additional/alternative methods to improve the capacity of a host cell to produce considerable amounts of recombinant proteins including potentially toxic proteins. Accordingly, the technical problem underlying the present invention is to comply with this need.

The present invention provides as a solution to the technical problem new means and methods to increase the yield of recombinant proteins in host cells which are simple and efficient and suitable for use in industrial methods. These means and methods are described herein, illustrated in the Examples, and reflected in the claims.

In particular, the present inventors uncovered a novel molecular mechanism that uncouples growth of the host cell from the production of a protein of interest. The double burden of a host cell caused by its proliferation and simultaneous expression of a heterologous protein reduces the yield of a protein of interest. In fact, the proliferation of the host cell during the production of a protein of interest poses an overload to the host cell resulting in a conflict in distribution of cellular resources. Thereby several unwanted side effects like generation of toxic by-products, reduced oxygen transfer and induction of a stress response are provoked, eventually resulting in a reorientation of the cellular metabolism constraining transcription and translation and potentially to cell death. Given that the cellular synthesis capacity is the basis of heterologous protein expression, one has to take the capacity of a host cell into account. In order to reduce or abolish the unwanted side effects of heterologous protein expression, the present inventors have developed an expression system that uncouples the production of the protein of interest from the proliferation of the host cell, thereby considerably reducing the burden on the host cell and increasing the yield of a protein of interest.

More particularly, the present inventors employ phage proteins that inhibit growth of the bacterial host cells by designing a host cell comprising a phage protein inhibiting growth of the bacterial host cell under the control of an inducible promoter. This allows switching OFF the host cells proliferation at will during the production process when the desired cell density is reached, while maintaining the host cells capability to produce the protein of interest as long as required resources are present. Hence, oxygen consumption, nutritional requirements and metabolic heat development are reduced, a stress response is circumvented and therefore sufficient resources for the production of the protein of interest are available. An additional problem of heterologous protein expression is the incorporation of the protein of interest in inclusion bodies resulting in a decreased solubility and thereby yield. This effect can be avoided by reducing cellular proliferation and induction temperature as shown by Vernet et al. (2010, Protein Expression and Purification, Vol. 77, Issue 1: 104-111) and thus by the present growth decoupled production system.

Phage proteins which inhibit cell growth have been found by the present inventors to be useful in uncoupling growth of a host cell and production of a protein of interest of said host cell. In fact, the phage protein ideally brings the host cell to halt, while an expression system that is insensitive to said phage protein can ideally fully exploit the protein production machinery of the halted host cell. For example, bacteriophage T7 uses its proteins gp0.7 and Gp2 to shut off E. coli RNA polymerase after infection. Immediately after infection early viral class I genes of bacteriophage T7, under control of bacterial promoters, are expressed, such as T7 RNA polymerase which is highly specific for viral genes under control of the T7 promoter. Among the class I genes is Gp0.7, which phosphorylates inter alia E. coli RNA polymerase resulting in transcription termination of early genes and in switching from host to viral RNA polymerase. Subsequently, the viral gene Gp2 is expressed, binding to and further inhibiting the beta subunit of the host RNA polymerase. Together Gp0.7 and/or Gp2 inhibit E. coli RNA polymerase and thereby cellular proliferation, resulting in a take-over of the bacterial protein synthesis machinery for viral purposes. Inhibition of E. coli RNA polymerase by Gp2 was shown by Studier and Moffat (1986, J. Mol. Biol., 189, 113-130), whereas they missed to disclose an impact on cellular proliferation.

Yet, apart from Gp0.7 and Gp2 further such phage proteins are available and have been used by the present inventors to show that their concept of using a phage protein for uncoupling growth of a host cell from its capacity of producing a protein of interest by using an expression system that is insensitive to such a phage protein. Further such phage proteins are, for example, Nun, Gp6, Gp8 or A*, Bacillus phage SPO1 GP40 SPO1 GP40, Staphylococcus phage G1 GP67, Thermus thermophilus phage P23-45 GP39, Enterobacteria phage PhiEco32 GP79, Xanthomonas oryzae bacteriophage Xp10 P7 protein, Enterobacteria phage T4 Alc protein, Enterobacteria phage T4Asia or Bacillus subtilis ykzG protein which are known in the art and are also described herein.

The present inventors adopted this functional principle for the purpose of producing a protein of interest by generating a bacterial host cell comprising (i) a phage protein under control of an inducible promoter which inhibits growth of the bacterial host cell, (ii) a heterologous RNA polymerase absent in the bacterial host cell and (iii) a protein of interest under control of a promoter recognized by said heterologous RNA polymerase, thereby facilitating to inhibit the cellular proliferation and concentrate the host cells capacity on the production of the protein of interest.

The present inventors used, exemplarily, a NEB10-beta E. coli host cell comprising the bacteriophage T7 protein Gp2 under control of an arabinose inducible promoter. Upon induction of Gp2 expression a strong dose dependent growth inhibition was observed. Subsequently, they used E. coli strain HMS174(DE3) TN7::<T7GFP> comprising a genomically integrated copy of the GFP gene under control of a T7 promoter and an expression vector encoding the Gp2 gene under control of an arabinose inducible promoter. They could show that the expression of GFP was increased upon concomitant expression of Gp2 in comparison to host cells solely expressing GFP.

It must be noted that as used herein, the singular forms "a", "an", and "the", include plural references unless the context clearly indicates otherwise. Thus, for example, reference to "an expression cassette" includes one or more of the expression cassettes disclosed herein and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

The term "about" or "approximately" as used herein means within 20%, preferably within 10%, and more preferably within 5% of a given value or range. It includes also the concrete number, e.g., about 20 includes 20.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well-known in the art. Generally, nomenclatures used in connection with techniques of biochemistry, enzymology, molecular and cellular biology, microbiology, genetics and protein and nucleic acid chemistry and hybridization described herein are those well-known and commonly used in the art.

The methods and techniques of the present invention are generally performed according to conventional methods well-known in the art and as described in various general and more specific references that are cited and discussed throughout the present specification unless otherwise indicated. See, e. g., Sambrook et al., Molecular Cloning: A Laboratory Manual, 3rd ed., Cold Spring Harbor Laboratory Press, Cold Spring Harbor, N.Y. (2001); Ausubel et al., Current Protocols in Molecular Biology, J, Greene Publishing Associates (1992, and Supplements to 2002); Handbook of Biochemistry: Section A Proteins, Vol I 1976 CRC Press; Handbook of Biochemistry: Section A Proteins, Vol II 1976 CRC Press. The nomenclatures used in connection with, and the laboratory procedures and techniques of, molecular and cellular biology, protein biochemistry, enzymology and medicinal and pharmaceutical chemistry described herein are those well-known and commonly used in the art.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The invention generally relates to a method of increasing the expression level of a protein of interest from a host cell in a production process. The invention relates particularly to improving the capacity of a bacterial host cell to express a protein of interest by expressing a phage protein during the production process which inhibits growth of the bacterial host cell. Decoupling growth of the bacterial host cell of manufacturing of the protein of interest during the production process reduces (i) the metabolic burden, (ii) oxygen demand, (iii) metabolic heat development, and (iv) avoids stress response caused by heterologous protein expression and thereby increases the capacity of a host cell to produce the protein of interest. The present invention also relates to uses of the host cell for protein expression, cell culture technology, and also to culturing host cells to produce a protein of interest.

Accordingly, it is an object of the present invention to provide a bacterial host cell which
(i) comprises under the control of an inducible promoter a nucleotide sequence encoding a protein from a phage which inhibits growth of said bacterial host cell; and
(ii) comprises a nucleotide sequence encoding a RNA polymerase which is heterologous for said bacterial host cell; and
(iii) comprises under the control of a promoter recognized by said RNA polymerase a nucleotide sequence which encodes a protein of interest.

The term "recombinant host cell" (or simply "host cell"), as used herein, is intended to refer to any prokaryotic cell, into which a nucleic acid comprising an expression cassette or vector has been introduced, i.e. which has been genetically-engineered. A preferred example of a prokaryotic host cell is *E. coli*. However, also *Pseudomonas* species, *Salmonella* species, *Bacillus* species, *Lactobacillus* species, *Corynebacterium* species, *Microbacterium* species or *Actinomycetes* species are envisaged. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell, preferably grown in culture.

In a preferred embodiment or the present invention the bacterial host cell is *E. coli*.

A skilled artisan is aware of genetic engineering techniques known in the art in order to generate a bacterial host cell of the present invention. For example, various kits are available for genetic engineering of bacterial host cell for the integration of nucleic acids comprising nucleotide sequences into a bacterial genome, either randomly or targeted; see e.g. Zhang et al. (1998), Nature Genetics 20, 123-128 or Sharan et al. (2009), Nature Protocols 4(2), 206-223. A skilled artisan is further aware of techniques for the transformation of bacterial host cell as well as with any other cloning technique which he can use for the generation of extrachromosomal elements such as plasmids, cosmids, bacmids, etc.

The term "growth" of the host cell as used herein means an increase of cell number due to cell division.

A promoter sequence as used herein is a non-coding expression control sequence preferably inserted nearby the start of the coding sequence of the expression cassette and regulates its expression. Put into a simplistic yet basically correct way, it is the interplay of the promoter with various specialized proteins called transcription factors that determine whether or not a given coding sequence may be transcribed and eventually translated into the actual protein encoded by the gene. It will be recognized by a person skilled in the art that any compatible promoter can be used for recombinant expression in host cells. The promoter itself may be preceded by an upstream activating sequence, an enhancer sequence or combination thereof. These sequences are known in the art as being any DNA sequence exhibiting a strong transcriptional activity in a cell and being derived from a gene encoding an extracellular or intracellular protein. It will also be recognized by a person skilled in the art that termination and polyadenylation sequences may suitably be derived from the same sources as the promoter.

The term "inducible promoter" as used herein refers to a promoter that regulates the expression of a operably linked gene or functional RNA in response to the presence or absence of an endogenous or exogenous stimulus. Such stimuli can be but are not limited to chemical compounds or environmental signals.

"Operably linked" expression control sequences refers to a linkage in which the expression control sequence is contiguous with the expression cassette, as well as expression control sequences that act in trans or at a distance to control expression of the expression cassette.

The term "nucleotide sequence" or "nucleic acid molecule" as used herein refers to a polymeric form of nucleotides (i.e. polynucleotide) which are usually linked from one deoxyribose or ribose to another. The term "nucleotide sequence" preferably includes single and double stranded forms of DNA or RNA. A nucleic acid molecule of this invention may include both sense and antisense strands of RNA (containing ribonucleotides), cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

In this regard, a nucleic acid being an expression product is preferably a RNA, whereas a nucleic acid to be introduced into a cell is preferably DNA, e.g. genomic DNA or cDNA.

The nucleic acid can be in any topological conformation. For instance, the nucleic acid can be single-stranded, double-stranded, triple-stranded, quadruplexed, partially double-stranded, branched, hairpinned, circular, or in a padlocked conformation.

A "polypeptide" refers to a molecule comprising a polymer of amino acids linked together by peptide bonds. Said term is not meant herein to refer to a specific length of the molecule and is therefore herein interchangeably used with the term "protein". When used herein, the term "polypeptide" or "protein" also includes a "polypeptide of interest" or "protein of interest" which is expressed by the expression cassettes or vectors or can be isolated from the host cells of the invention. A protein of interest also includes proteins which may potentially be harmful or even toxic for host cells.

Examples of a protein of interest are enzymes more preferably an amylolytic enzyme, a lipolytic enzyme, a proteolytic enzyme, a cellulytic enzyme, an oxidoreductase or a plant cell-wall degrading enzyme; and most preferably an enzyme having an activity selected from the group consisting of aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinase, peroxidase, phytase, phenoloxidase, polyphenoloxidase, protease, ribonuclease, transferase, transglutaminase, and xylanase. Furthermore, a protein of interest may also be a growth factor, cytokine, receptors, receptor ligands, therapeutic proteins such as interferons, BMPs, GDF proteins, fibroblast growth factors, peptides such as protein inhibitors, membrane proteins, membrane-associated proteins, peptide/protein hormones, peptidic toxins, peptidic antitoxins, antibody or functional fragments thereof such as Fab or F(ab)$_2$ or derivatives of an antibody such as bispecific antibodies (for example, scFvs), chimeric antibodies, humanized antibodies, single domain antibodies such as Nanobodies or domain antibodies (dAbs) or an anticalin and others.

A "polypeptide" as used herein encompasses both naturally-occurring and non-naturally-occurring proteins, and fragments, mutants, derivatives and analogs thereof. Polypeptides may be a polypeptide homologous (native) or heterologous to the host cell. The polypeptide of interest may also encompass a polypeptide native to the host cell, which is encoded by a nucleic acid sequence, which expression is controlled by one or more control sequences foreign to the nucleic acid sequence encoding the polypeptide. Polypeptides may be of any length. Polypeptides include proteins and/or peptides of any activity or bioactivity. A "peptide" encompasses analogs and mimetics that mimic structural and thus biological function.

Polypeptides may further form dimers, trimers and higher oligomers, i.e. consisting of more than one polypeptide molecule. Polypeptide molecules forming such dimers, trimers etc. may be identical or non-identical. The corresponding higher order structures are consequently termed homo- or heterodimers, homo- or heterotrimers etc.

Further, a polypeptide may comprise a number of different domains each of which has one or more distinct activities.

The nucleic acid sequence encoding a protein of the present invention or protein of interest may be obtained from any prokaryotic, eukaryotic, or other source.

As described herein, a nucleotide sequence encoding a protein of the present invention or protein of interest is preferably regulated by a promoter. Said promoter is preferably specifically transcribed by an RNA polymerase that is heterologous for said host cell and the expression of which may be inducible. However, said RNA polymerase may also be constitutively expressed.

When used herein, the term "growth of a bacterial host cell" means that a host cell is at least impaired in its growth compared to a host cell which does not express a phage protein that inhibits growth of a bacterial host cell, and which comprises a nucleotide sequence encoding a RNA polymerase which is heterologous for said bacterial host cell and, which comprises under the control of a promoter recognized by said RNA polymerase a nucleotide sequence which encodes a protein of interest. Notably, it is not excluded that such a host cell which does not express said phage protein nevertheless comprises under the control of an inducible promoter a nucleotide sequence encoding a protein from a phage which inhibits growth of said bacterial host cell. In fact, such a host cell is a preferred reference cell, e.g. for determining the impairment of growth as described before. Put differently, when impairment of growth should be determined, the skilled artisan can easily compare a host cell of the present invention when expression of said phage protein is induced versus such a host when expression of said phage protein is not induced.

When "growth of a bacterial host cell" is inhibited as described herein, growth includes preferably transcription, DNA-replication and/or cell division. Accordingly, it is preferred that a phage protein, particularly one or more of the phage proteins described herein, inhibits transcription, DNA-replication and/or cell division.

A "phage protein" when referred to herein is a protein from a (bacterio)phage. A phage infects bacteria and is able to replicate in said bacterium. When infecting a bacterium and replicating in said bacterium a phage may have one or more proteins that inhibit growth of said bacterium, e.g., by inhibiting transcription, DNA-replication and/or cell division in order to fully exploit the protein synthesis machinery of said bacterium.

Accordingly, the present invention can be put into practice with any phage protein that effects the inhibition of the growth of the bacterial host cell by causing, e.g. a host transcription shut-off. In this case the bacterial host cell comprises under the control of an inducible promoter a nucleotide sequence encoding a protein from a phage which causes a transcription shut-off of said bacterial host cell. The term "host transcription shut-off" as used herein relates to the inhibition of transcription of the bacterial host cell. Proteins that can be used to cause a host transcription shut-off are described herein, such as Gp2, GP0.7, Nun, Gp6, Gp8, A*,YkzG Epsilon-Subunit. However, further proteins that effect a host transcription shut-off may be used as well to put the present invention into practice. Such proteins are for example *Bacillus* phage SPO1 GP40 SPO1 GP40, *Staphylococcus* phage G1 GP67, *Thermus thermophilus* phage P23-45 GP39, Enterobacteria phage PhiEco32 GP79, *Xanthomonas oryzae* bacteriophage Xp10 P7 protein, Enterobacteria phage T4 Alc protein, Enterobacteria phage T4 Asia protein.

Exemplarily, Example 1 in conjunction with FIG. 1 illustrates that inhibition of the host cell's transcription, by induced expression of the phage protein Gp2 that inhibits bacterial host cell RNA polymerase, inhibits growth of the host cell as a function of the inducer molecule arabinose.

Accordingly, the phage protein of the present invention is preferably (i) a protein which inhibits bacterial host cell RNA polymerase, wherein said protein is
  (a) a protein having the amino acid sequence shown in Seq Id No: 1 or a fragment thereof which inhibits bacterial host cell RNA polymerase; or
  (b) a protein having an amino acid sequence which has an identity of 40% or more, such as 50%, 60%, 70%, 80% or 90% to the amino acid sequence shown in Seq Id No: 1 and which inhibits bacterial host cell RNA polymerase;

(ii) a protein which inhibits bacterial host cell RNA polymerase, wherein said protein is
  (a) a protein having the amino acid sequence shown in Seq Id No: 2 or a fragment thereof which inhibits bacterial host cell RNA polymerase; or
  (b) a protein having an amino acid sequence which has an identity of 40% or more, such as 50%, 60%, 70%, 80% or 90% to the amino acid sequence shown in Seq Id No: 2 and which inhibits bacterial host cell RNA polymerase;

(iii) a protein which phosphorylates bacterial host cell RNA polymerase, wherein said protein is
  (a) a protein having the amino acid sequence shown in Seq Id No: 3 or a fragment thereof which phosphorylates bacterial host cell RNA polymerase; or
  (b) a protein having an amino acid sequence which has an identity of 40% or more, such as 50%, 60%, 70%, 80% or 90% to the amino acid sequence shown in Seq Id No: 3 and which phosphorylates bacterial host cell RNA polymerase;

(iv) a protein which inhibits bacterial host cell DNA replication, wherein said protein is
  (a) a protein having the amino acid sequence shown in Seq Id No: 4 or a fragment thereof which inhibits bacterial host cell DNA replication; or
  (b) a protein having an amino acid sequence which has an identity of 40% or more, such as 50%, 60%, 70%, 80% or 90% to the amino acid sequence shown in Seq Id No: 4 and which inhibits bacterial host cell DNA replication;

(v) a protein which inhibits bacterial host cell DNA replication, wherein said protein is
  (a) a protein having the amino acid sequence shown in Seq Id No: 5 or a fragment thereof which inhibits bacterial host cell DNA replication; or
  (b) a protein having an amino acid sequence which has an identity of 40% or more, such as 50%, 60%, 70%, 80% or 90% to the amino acid sequence shown in Seq Id No: 5 and which inhibits bacterial host cell DNA replication; or (vi) a protein which inhibits bacterial host cell DNA replication, wherein said protein is
  (a) a protein having the amino acid sequence shown in Seq Id No: 6 or a fragment thereof which inhibits bacterial host cell DNA replication; or
  (b) a protein having an amino acid sequence which has an identity of 40% or more, such as 50%, 60%, 70%, 80% or 90% to the amino acid sequence shown in Seq Id No: 6 and which inhibits bacterial host cell DNA replication;

(vii) a protein which inhibits bacterial host cell RNA polymerase, wherein said protein is
  (a) a protein having the amino acid sequence shown in Seq Id No: 7 or a fragment thereof which inhibits bacterial host cell RNA polymerase; or
  (b) a protein having an amino acid sequence which has an identity of 40% or more, such as 50%, 60%, 70%, 80% or 90% to the amino acid sequence shown in Seq Id No: 7 and which inhibits bacterial host cell RNA polymerase;

(viii) a protein which causes host transcription shut-off, wherein said protein is
  (a) a protein having the amino acid sequence shown in Seq Id No: 8, 9, 10, 11, 12, 13, 14 or a fragment thereof which causes host transcription shut-off; or
  (b) a protein having an amino acid sequence which has an identity of 40% or more, such as 50%, 60%, 70%, 80% or 90% to the amino acid sequence shown in Seq Id No: 8, 9, 10, 11, 12, 13 or 14 and which causes host transcription shut-off.

In a further preferred embodiment of the present invention said nucleotide sequence encoding a protein from a phage which inhibits growth of said bacterial host cell, said nucleotide sequence encoding said RNA polymerase, said nucleotide sequence encoding a protein of interest, is integrated into the genome of said host cell or is comprised by an extrachromosomal vector.

The term "vector" as used herein refers to a nucleic acid sequence into which an expression cassette comprising a gene of the present invention or gene encoding the protein of interest may be inserted or cloned. Furthermore, the vector may encode an antibiotic resistance gene conferring selection of the host cell. Preferably, the vector is an expression vector.

The vector may be capable of autonomous replication in a host cell (e. g., vectors having an origin of replication which functions in the host cell). The vector may have a linear, circular, or supercoiled configuration and may be complexed with other vectors or other material for certain purposes.

Vectors used herein for expressing an expression cassette comprising a gene of the present invention or gene encoding the protein of interest usually contain transcriptional control elements suitable to drive transcription such as e.g. promoters, enhancers, polyadenylation signals, transcription pausing or termination signals as elements of an expression cassette. For proper expression of the polypeptides, suitable translational control elements are preferably included in the vector, such as e.g. 5' untranslated regions leading to 5' cap structures suitable for recruiting ribosomes and stop codons to terminate the translation process. In particular, the nucleotide sequence serving as the selectable marker genes as well as the nucleotide sequence encoding the protein of interest can be transcribed under the control of transcription elements present in appropriate promoters. The resultant transcripts of the selectable marker genes and that of the protein of interest harbour functional translation elements that facilitate substantial levels of protein expression (i.e. translation) and proper translation termination.

The vector may comprise a polylinker (multiple cloning site), i.e. a short segment of DNA that contains many restriction sites, a standard feature on many plasmids used for molecular cloning. Multiple cloning sites typically contain more than 5, 10, 15, 20, 25, or more than 25 restrictions sites. Restriction sites within an MCS are typically unique (i.e., they occur only once within that particular plasmid). MCSs are commonly used during procedures involving molecular cloning or subcloning.

One type of vector is a plasmid, which refers to a circular double stranded DNA loop into which additional DNA segments may be introduced via ligation or by means of restriction-free cloning. Other vectors include cosmids, bacterial artificial chromosomes (BAC), yeast artificial chromosomes (YAC) or mini-chromosomes. Another type of vector is a viral vector, wherein additional DNA segments may be ligated into the viral genome.

The invention further relates to a vector that can be integrated into the host cells genome and thereby replicates along with the host cells genome. The expression vector may comprise a predefined restriction site, which can be used for linearization of the vector nucleic acid prior to transfection. The skilled person knows how to integrate into the genome. For example, it is important how to place the linearization restriction site, because said restriction site determines where the vector nucleic acid is opened/linearized and thus determines the order/arrangement of the expression cassettes when the construct is integrated into the genome of the host cell.

An antibiotic resistance gene, in accordance with the invention, means a gene which provides the transformed cells with a selection advantage (e.g. resistance against an antibiotic) by expressing the corresponding gene product. The gene product confers a characteristic to the cell expressing the antibiotic resistance gene that allows it to be distinguished from cells that do not express the antibiotic resistance gene (i.e. selection of cells) if the antibiotic, to which the gene product confers resistance to, is applied to the cell culture medium. Resistance by the gene product to the cell may be conferred via different molecular mechanisms (e.g. inactivation of the drug, increased efflux).

The expression cassette comprising a gene of the present invention or gene encoding the protein of interest is inserted into the expression vector as a DNA construct. This DNA construct can be recombinantly made from a synthetic DNA molecule, a genomic DNA molecule, a cDNA molecule or a combination thereof. The DNA construct is preferably made by ligating the different fragments to one another according to standard techniques known in the art.

The expression cassette comprising a gene of the present invention or gene encoding the protein of interest may be part of the expression vector. Preferably, the expression vector is a DNA vector. The vector conveniently comprises sequences that facilitate the proper expression of the gene encoding the protein of interest and the antibiotic resistance gene. These sequences typically comprise but are not limited to promoter sequences, transcription initiation sites, transcription termination sites, and polyadenylation functions as described herein.

The expression cassettes may comprise an enhancer and/or an intron. Usually, introns are placed at the 5' end of the open reading frame. Accordingly, an intron may be comprised in the expression cassette for expressing the polypeptide of interest in order to increase the expression rate. Said intron may be located between the promoter and or promoter/enhancer element and the 5' end of the open reading frame of the polypeptide to be expressed. Several suitable introns are known in the state of the art that can be used in conjunction with the present invention.

The expression cassette or vector according to the invention which is present in the host may either be integrated into the genome of the host or it may be maintained in some form extrachromosomally.

Furthermore, the expression cassettes may comprise an appropriate transcription termination site. This, as continued transcription from an upstream promoter through a second transcription unit may inhibit the function of the downstream promoter, a phenomenon known as promoter occlusion or transcriptional interference. This event has been described in both prokaryotes and eukaryotes. The proper placement of transcriptional termination signals between two transcription units can prevent promoter occlusion. Transcription termination sites are well characterized and their incorporation in expression vectors has been shown to have multiple beneficial effects on gene expression.

The terms "5'" and "3'" used herein refer to a convention used to describe features of a nucleotide sequence related to either the position of genetic elements and/or the direction of events (5' to 3'), such as e.g. transcription by RNA polymerase or translation by the ribosome which proceeds in 5' to 3' direction. Synonyms are upstream (5') and downstream (3'). Conventionally, nucleotide sequences, gene maps, vector cards and RNA sequences are drawn with 5' to 3' from left to right or the 5' to 3' direction is indicated with arrows, wherein the arrowhead points in the 3' direction. Accordingly, 5' (upstream) indicates genetic elements positioned towards the left hand side, and 3' (downstream) indicates genetic elements positioned towards the right hand side, when following this convention.

The term "expression" as used herein means the transcription of a nucleotide sequence. Said nucleotide sequence encodes preferably a protein. Accordingly, said term also includes the production of mRNA (as transcription product from a nucleotide sequence) and translation of this mRNA to produce the corresponding gene product, such as a polypeptide, or protein.

The RNA polymerase is advantageously heterologous to the bacterial host cell which comprises a nucleotide sequence encoding said RNA polymerase. "Heterologous" means that the RNA polymerase is not naturally occurring in said bacterial host cell, i.e., said bacterial host cell does not naturally comprise said RNA polymerase, unless a nucleotide sequence encoding said RNA polymerase is introduced in said bacterial host cell in accordance with the teaching of the present invention by means and methods known in the art. The RNA polymerase is thus ideally insensitive to a phage protein which inhibits growth of said bacterial host cell.

Preferably, the RNA polymerase is bacteriophage T3 RNA polymerase, T7 bacteriophage RNA polymerase, engineered orthogonal T7 RNA polymerase, bacteriophage SP6 RNA polymerase or bacteriophage Xp10 RNA polymerase. Further RNA polymerases, such as engineered orthogonal T7 polymerases are described in Temme et al. (2012), Nucleic Acids Research 40(17), 8773-8781.

In a preferred embodiment of the present invention the nucleotide sequence encoding the RNA polymerase is under the control of an inducible or constitutive promoter. Examples of inducible promoters are described herein in the context of an inducible promoter which controls a nucleotide sequence encoding a protein from a phage which inhibits growth of said bacterial host cell. These inducible promoters are also preferred examples for an inducible promoter that controls the RNA polymerase as described herein below.

Preferably, the inducible promoter which controls a nucleotide sequence encoding a protein from a phage which inhibits growth of said bacterial host cell is regulated by arabinose, IPTG, tryptophane, xylose, rhamnose, phosphate or phage lambda cI protein.

As regards inducible promoters that control a nucleotide sequence encoding a protein from a phage which inhibits growth of said bacterial host cell as or that control a nucleotide sequence encoding said RNA polymerase, it is preferred that the same inducible promoters are applied. Preferred examples are described herein. This preferred embodiment allows to simultaneously induce expression of the phage protein and the RNA polymerase in order to uncouple growth and protein production. However, of course, also different inducible promoters can be used in accordance with the teaching of the present invention.

In a preferred embodiment of the bacterial host cell, said host cell has a non-functional arabinose operon.

The present invention also provides a preparation of a bacterial host cell which
(i) comprises under the control of an inducible promoter a nucleotide sequence encoding a protein from a phage as defined herein which inhibits growth of said bacterial host cell; and
(ii) comprises a nucleotide sequence encoding an RNA polymerase which is heterologous for said bacterial host cell.

A "preparation" of a bacterial host cell" as used herein is any preparation which is advantageously free of intact, living bacterial host cells, but which has the capability of transcribing and translating a nucleotide sequence encoding a protein of interest, whereby said nucleotide sequence is under the control of a promoter recognized by the RNA polymerase which is heterologous for said bacterial hoist cell from which the preparation is derived from. Such a preparation can, e.g., be prepared by mild lysis of bacterial host cells or by mechanical forces such as subjecting such bacterial host cells to a French press.

The present invention further comprises a method for the production of a host cell as described herein, comprising transforming a bacterial host cell with a nucleotide sequence encoding a protein from a phage which inhibits growth of said bacterial host cell as defined herein, a nucleotide sequence encoding T7 RNA polymerase, and a nucleotide sequence encoding a protein of interest.

The term "transforming" as used herein means alteration of the genotype of a host cell by introducing a nucleotide sequence. The nucleotide sequence does not necessarily originate from a different source, but it will, at some point, have been external to the cell into which it is to be introduced.

In a further aspect the present invention comprises a method for the production of a protein of interest, comprising culturing the bacterial host cell as described herein under suitable conditions and obtaining said protein of interest.

A large number of suitable methods exist in the art to produce polypeptides in host cells of the invention. Conveniently, the produced protein is harvested from the culture medium, lysates of the cultured host cell or from isolated (biological) membranes by established techniques. For example, an expression cassette comprising, inter alia, the nucleotide sequence encoding the protein of interest can be synthesized by PCR and inserted into the expression vector. Subsequently, a cell may be transformed with the expression vector. Thereafter, the cell is cultured to produce/express the desired protein(s), which is/are isolated and purified. For example, the product may be recovered from the host cell and/or culture medium by conventional procedures including, but not limited to, cell lysis, breaking up host cells, centrifugation, filtration, ultra-filtration, extraction, evaporation, spray drying or precipitation. Purification may be performed by a variety of procedures known in the art including, but not limited to, chromatography (e.g. ion exchange, affinity, hydrophobic, chromatofocusing, and size exclusion), electrophoretic procedures (e.g., preparative isoelectric focusing), differential solubility (e.g. ammonium sulfate precipitation) or extraction.

"Isolating the protein of interest" refers to the separation of the protein of interest produced during or after expression of the vector introduced. In the case of proteins or peptides as expression products, said proteins or peptides, apart from the sequence necessary and sufficient for the protein to be functional, may comprise additional N- or C-terminal amino acid sequences. Such proteins are referred to as fusion proteins.

When a polypeptide of interest is expressed in a host cell of the invention, it may be necessary to modify the nucleotide sequence encoding said polypeptide by adapting the codon usage of said nucleotide sequence to meet the frequency of the preferred codon usage of said host cell. As used herein, "frequency of preferred codon usage" refers to the preference exhibited by the host cell of the invention in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG).

A tag may be used to allow identification and/or purification of the protein of interest. Accordingly, it is preferred that a protein of interest comprises a tag. Hence, a nucleotide sequence encoding a protein of interest preferably also encodes a tag which is advantageously genetically fused in frame to the nucleotide sequence encoding said protein of interest. Said tag may be at the C- or N-terminus of said protein of interest. Examples of tags that may be used in accordance with the invention include, but are not limited to, HAT, FLAG, c-myc, hemagglutinin antigen, His (e.g., 6×His) tags, flag-tag, strep-tag, strepII-tag, TAP-tag, chitin binding domain (CBD), maltose-binding protein, immunoglobulin A (IgA), His-6-tag, glutathione-S-transferase (GST) tag, intein and streptavidine binding protein (SBP) tag.

In a further embodiment the present invention provides a method of increasing the yield of a protein of interest, comprising culturing a bacterial host cell as defined herein under suitable conditions and obtaining said protein of interest.

The term "yield" as used herein refers to the amount of protein of interest which is, for example, harvested from the recombinant host cell, and increased yields can be due to increased amounts of production or secretion of the protein of interest or model protein by the host cell. Yield may be presented by mg protein/g biomass (measured as dry cell weight or wet cell weight) of a host cell. The term "titer" when used herein refers similarly to the amount of produced protein of interest or model protein, presented as g protein/L culture broth (including the cells). An increase in yield can be determined when the yield obtained from a recombinant host cell the proliferation of which has been inhibited temporarily during the production process is compared to the yield obtained from a host cell the proliferation of which was not modified.

Exemplarily, Example 3 in conjunction with FIG. 3 illustrates that the induced expression of the phage protein Gp2 results in an increased expression of the model protein GFP.

Preferably, the methods described herein include the culturing steps
(a) growing the bacterial cells to a density of at least 20 g/L cell dry mass (CDM);
(b) inducing expression of the nucleotide sequence encoding a phage protein which inhibits growth of the host cell;
(c) feeding bacterial cells with a constant linear feed rate that would allow an initial growth rate of 0.05 $h^{-1}$; and
(d) further culturing said bacterial cells for at least 12 hours.

In a further preferred embodiment the present invention comprises a method for increasing the yield of a protein of interest, comprising transforming a bacterial host which comprises a nucleotide sequence encoding a RNA polymerase being heterologous for said bacterial host cell and a nucleotide sequence which encodes a protein of interest, said nucleotide sequence is under the control of a promoter which is recognized by said RNA polymerase with a nucleotide sequence under the control of an inducible promoter, said nucleotide sequence encoding a protein from a phage which inhibits growth of said bacterial host cell.

A method for the production of a protein of interest, comprising bringing into contact under suitable conditions the preparation as described herein with a nucleotide sequence comprising under the control of a promoter recognized by an RNA polymerase as defined herein a nucleotide sequence which encodes a protein of interest.

Furthermore, the methods described herein relate to a protein of interest that is toxic for cells, adversely affects viability, cell growth and/or cell division.

The term "toxic" as used herein means that the protein of interest or derivative thereof or a precursor thereof has an adverse effect on the host cell upon its expression or is metabolized to a derivative that has an adverse effect on the host cell. An example of an adverse effect is growth inhibition. The term also includes death of the host cell.

In a further embodiment the methods of the present invention comprise modifying the protein of interest and/or formulating the protein of interest into a composition which includes at least one additional component.

The term "modifying the protein of interest" as used herein may be but is not limited to, fusion with another protein, addition of a label, truncating the protein of interest, addition of posttranslational modifications, e.g. acetylation, glucosylation, biotinylation, oxidation, nucleotide addition, amidation, amino acid addition, alkylation, palmitoylation, and others, crosslinking the protein of interest, chemical modification of the protein of interest, e.g. pegylation, convertion of amines to sulfhydryls, blocking of sulfhydryl groups or others. A "label" may be a fluorescent label, a bioluminescent label, a radioactive label, an enzymatic label, and the like.

It is also envisioned herein that the methods of the present invention may be used for modifying the protein of interest by incorporation of compounds into the protein of interest. The incorporation of said compounds may be used for labeling of the protein of interest. This may be especially useful for protein structure analysis. Examples for said compounds are $C_{12}$, $N_{15}$, $D_2O$ or any combination thereof. The methods of the present invention provide the advantage that said compounds will be exclusively used in the production of the protein of interest but not in the production of cellular proteins. Hence, less labeling compounds will be required for labeling a protein of interest.

Furthermore, the methods of the present invention may be used for modifying the protein of interest by incorporation of non-canonical amino acids into the protein of interest. One example of such a non-canonical amino acid are fluoro amino acids (e.g. 4-fluoro-L-threonine), which may be used for fluorinating a protein of interest. A non-canonical amino acid may be incorporated globally in the protein by residue-specific substitution of one or more canonical amino acids by their non-canonical analogs or site-specific by inserting an amber stop codon in-frame into the coding sequence of the protein of interest. Said amber stop codon is recognized by an orthogonal tRNA (e.g. by a mis-acylated suppressor tRNA), wherein said orthogonal tRNA is predominantly charged with a non-canonical amino acid by an orthogonal tRNA synthetase.

The term "formulating the protein of interest into a composition" as used herein means that the protein of interest is mixed with one or more components that, e.g. protect the protein of interest from degradation, denaturation, harsh environments or being hydrolyzed by proteases or that dilute the protein of interest or that improve the pharmaceutical activity of the protein of interest when administered as a drug to a patient or that are advantageous in the manufacturing process or others.

In a preferred embodiment of the present invention, said protein of interest is modified with a label.

The term "label" as used herein may be but is not limited to a tag, e.g. Biotin, Strep-tag II, FLAG-tag, HA-tag, Myc-tag, poly(His)-tag, glutathione-S-transferase (GST), maltose binding protein (MBP), chitin binding protein (CBP), and others, or a fluorescent probe, e.g. GFP, RFP, BFP, YFP, mCherry, FITC, TRITC, DyLight Fluors, PE, Quantum dots, Alexa fluors, and others, or an enzyme, e.g. alkaline phosphatase, horseradish peroxidase, glucose oxidase, beta-galctosidase, and others, or an active site probe, e.g. Desthiobiotin-FP Serine Hydrolase Probe and others.

A method for the production of a compound of interest, comprising culturing the bacterial host cell as described herein and adding a compound that is to be converted and/or used by said bacterial host cell for the production of said compound of interest.

The term "compound of interest" as used herein may be but is not limited to precursors or building block molecules for plastics, such as conversion of bicyclo[3.2.0]-hept-2-en-6-one to lactones, alcohols, such as conversion of prochiral carbonyl compounds to chiral, conversion of ferulic acid to coniferyl aldehyde to coniferyl alcohol, or conversion of eugenol to ferulic acid to coniferyl alcohol to vanillin.

The invention further relates to the use of the host cell or the preparation as described herein for the production of a protein of interest.

In a further embodiment the invention relates to the use of the host cell or the preparation as described herein for increasing the yield of a protein of interest.

In a further embodiment the invention relates to the use of a nucleotide sequence encoding a phage protein as defined herein for increasing the yield of a protein of interest in a host cell.

The use of a phage protein as described herein, wherein the protein of interest is under the control of a T7 promoter and said host cell comprises a nucleotide sequence encoding T7 RNA polymerase.

FIGURES

FIG. 1: The induced expression of Gp2 inhibits the host cell growth of *E. coli* strain NEB10-beta in a dose-dependent manner.

The Gp2 encoding sequence under control of an arabinose-inducible promoter was cloned in the low-copy f-plasmid pKLJ12 (Jones and Keasling (1998), Biotechnol Bioengineer 59: 659-665). The plasmid pKLJ12+Gp2 was transformed in *E. coli* strain NEB10-beta which comprises an araD139 mutation. Consequently, NEB10-beta is not capable of metabolizing the inducer arabinose. Addition of different concentrations of arabinose and thereby expression of Gp2 cause an inhibition of proliferation in a dose-dependent manner.

Figure 2:
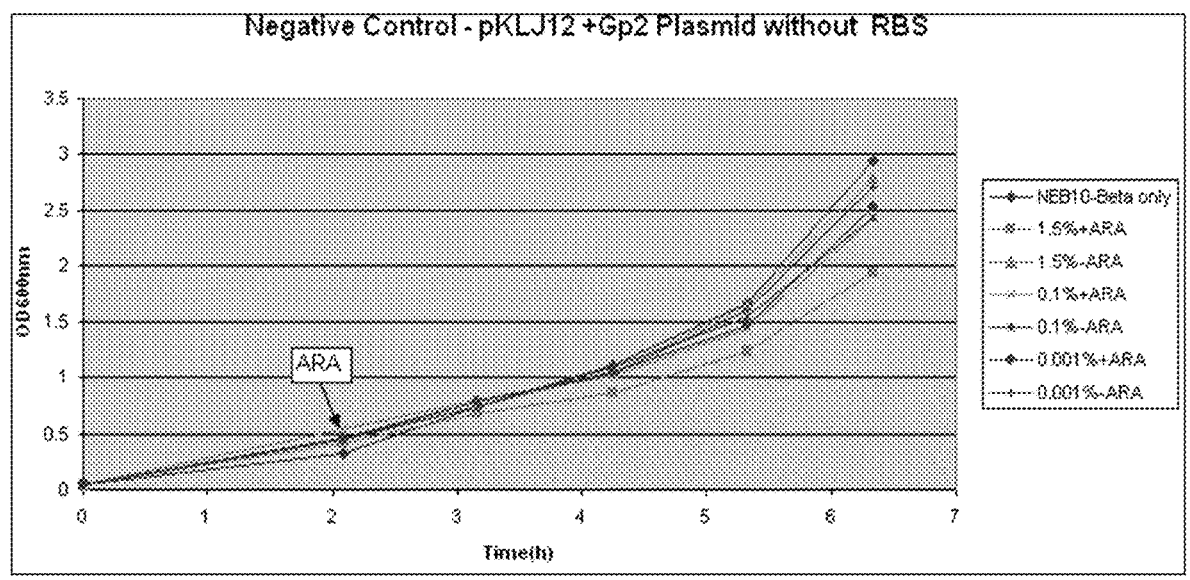

FIG. 2: Addition of arabinose has no effect on host cell growth.

In order to exclude any effect of the compound arabinose on host cell growth a derivative of plasmid pKLJ12+Gp2 lacking the ribosome binding site of the Gp2 expression cassette has been employed. Consequently, expression of Gp2 cannot be induced and hence no difference in proliferation was observed with or without arabinose.

FIG. 3: The induced expression of Gp2 increases the expression level of the model protein GFP.

*E. coli* strain HMS174(DE3) TN7::<T7GFP>, comprising the GFP encoding sequence under control of a T7 promoter and T7 RNA polymerase under control of an IPTG-inducible promoter, was transformed with the plasmid pKLJ12+Gp2 which harbors the Gp2 encoding sequence under control of an arabinose-inducible promoter. Three consecutive experiments showed that host cells induced with IPTG and arabinose, expressing T7 RNA polymerase and Gp2, expressed GFP to a higher extent compared to host cells that were induced with IPTG, only, and therefore expressed T7 RNA polymerase but not Gp2.

FIG. 4: Expression of Gp2 from the pKLJ12+Gp2 insert without the vector increases the GFP expression.

*E. coli* strain HMS174(DE3) TN7::<T7GFP>, comprising the GFP encoding sequence under control of a T7 promoter and T7 RNA polymerase under control of an IPTG-inducible promoter, was transformed with the insert of pKLJ12+Gp2 comprising the Gp2 expression cassette. In two out of three cases the transformation of the Gp2 expression cassette resulted in an increased GFP expression 3 h after IPTG induction.

FIG. 5: Amino acid sequences of exemplary, but nevertheless preferred (phage) proteins which inhibit growth of a bacterial host cell.

Figure 6:
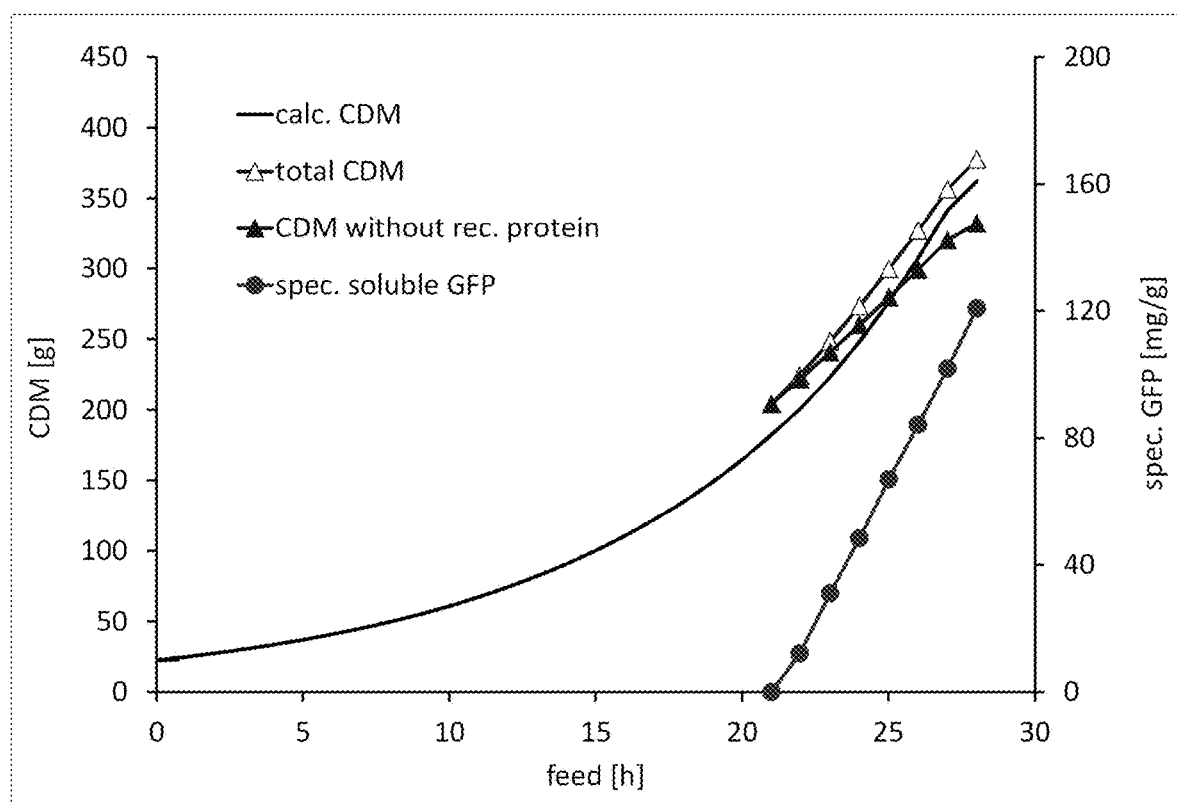

FIG. 6: Reference fermentation process lacking Gp2 expression.

In the reference fermentation process Gp2 is not expressed and therefore cells continue growing during production of the model protein GFP, as expected. Consequently, total CDM (cell dry mass) and CDM without recombinant protein increase during the entire fermentation process. Induced expression of GFP results in a constant increases of both, specific soluble GFP and total soluble GFP during the entire fermentation process.

Figure 7:
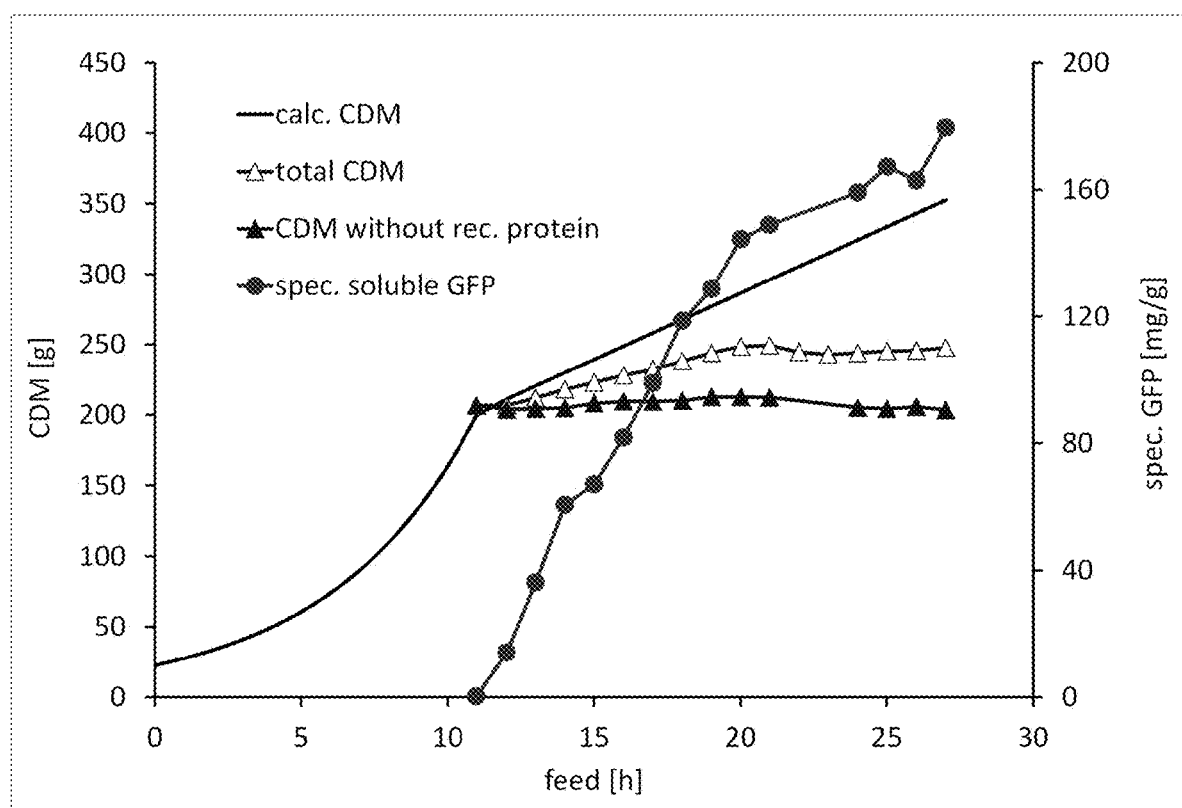

FIG. 7: Example fermentation process in which growth and protein production have been uncoupled by Gp2 expression.

In the example fermentation process Gp2 expression causes a growth arrest of the cells. Consequently, CDM without recombinant protein remains constant upon induction of Gp2 expression at the time point 11 h whereas total CDM increases moderately due to the production of recombinant GFP. Both, specific soluble GFP and total soluble GFP increase during the course of the fermentation process despite growth arrest of the cells.

FIG. 8: Expression of Gp2 increases the expression level of GFP and the ratio of GFP to soluble host cell protein (HCP) in the supernatant.

The coomassie stained SDS PAGE gel shows an increase of soluble GFP in the supernatant (S) using the growth decoupled system (*E. coli* BL21 (DE3) with genome integrated inducible Gp2 protein compared to a standard system (*E. coli* BL21 (DE3) without genome integrated inducible Gp2 protein). Furthermore, the relative amount of GFP to HCP (excluding Lysozyme) in the supernatant is considerably higher using the growth decoupled system compared to a standard system. Additionally, solubility of GFP is improved by using the growth decoupled system compared to a standard system.

Figure 9:
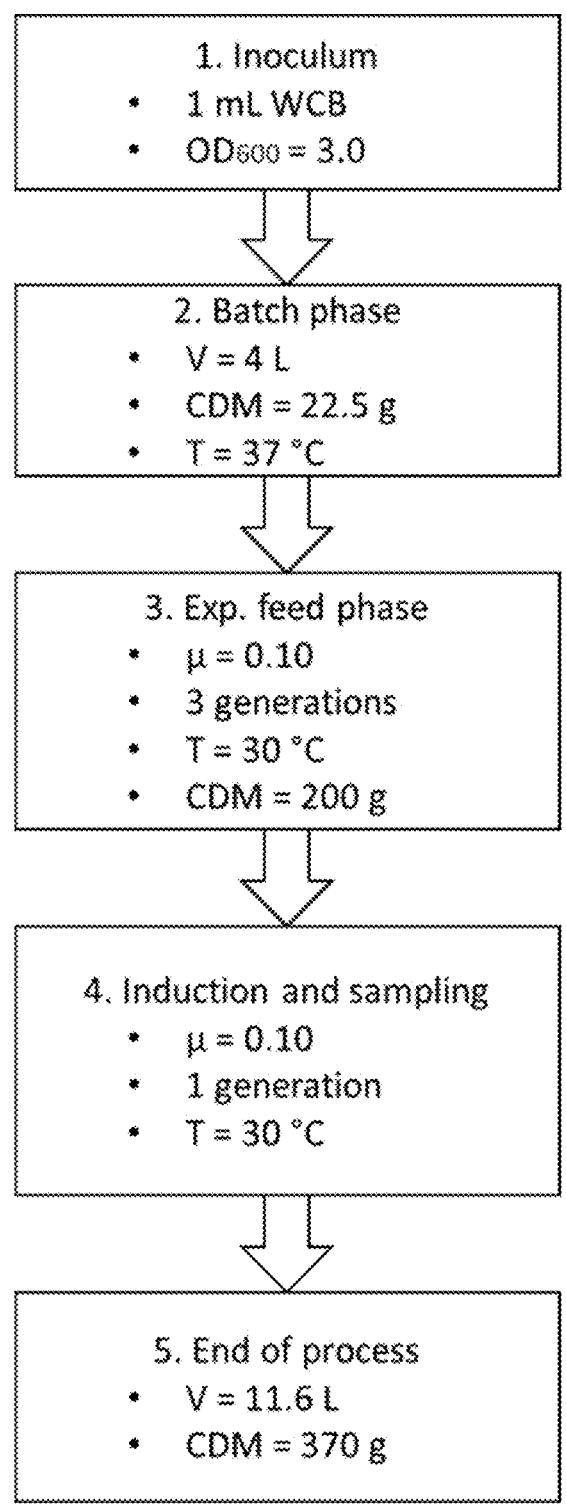

FIG. 9: Reference process scheme. Induction with 0.1 mM IPTG.

Figure 10:
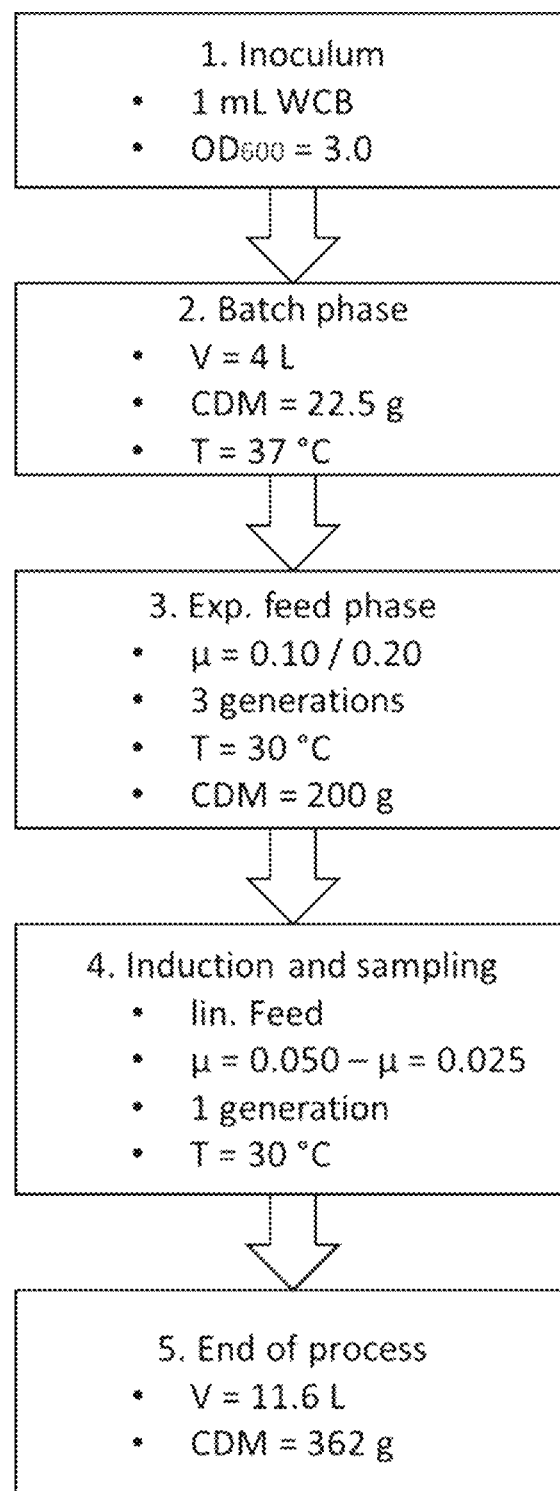

FIG. 10: Process scheme of fed-batch cultivations and induction strategy with Arabinose and IPTG.

Figure 11:
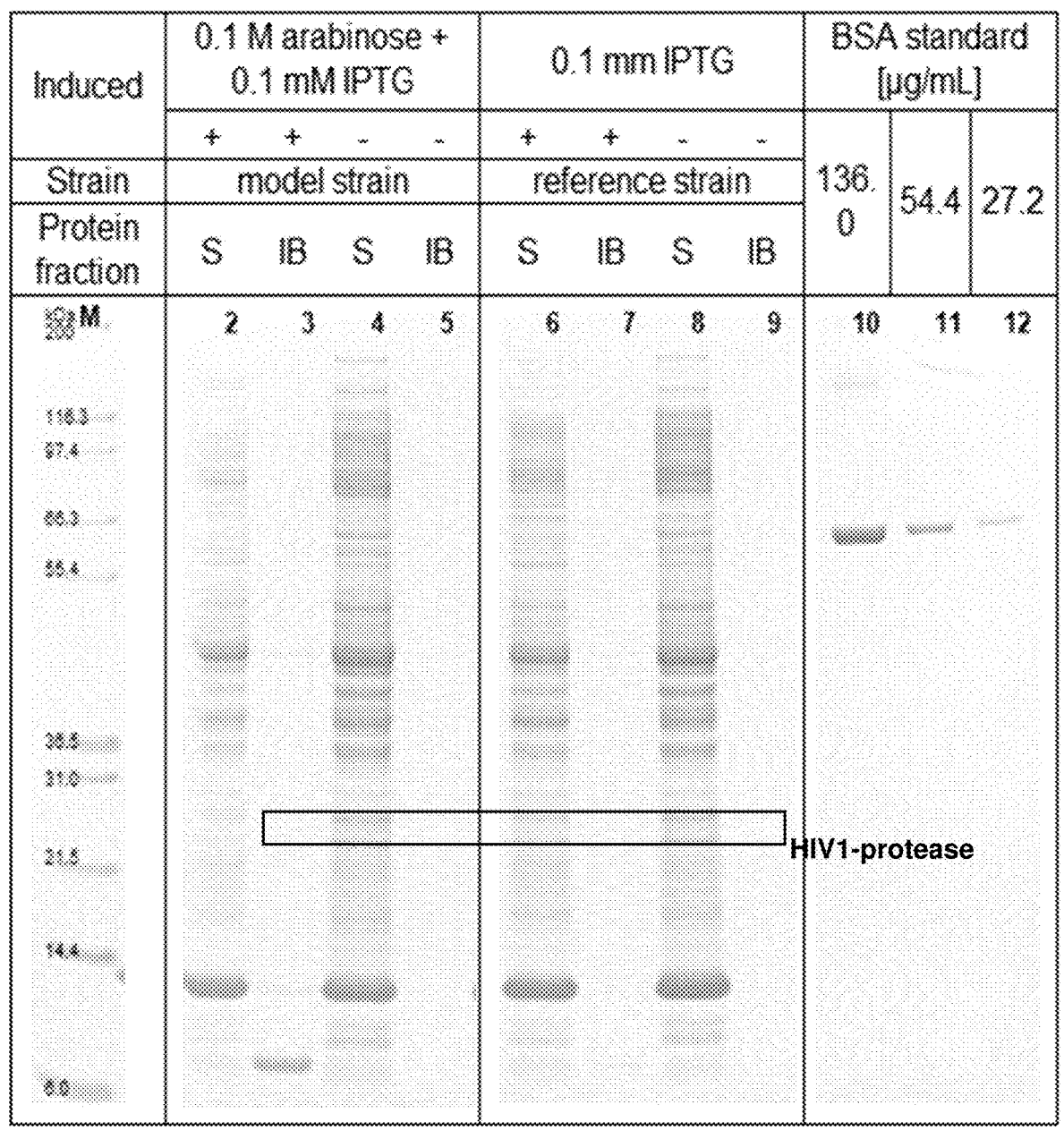

FIG. 11: SDS page analysis of shake flask cultivations of BL21 (DE3)::TN7(Gp2ΔAra)pET30(HIV1-protease) and BL21(DE3)pET30(HIV1-protease).

Comparison of induced and non-induced samples of reference strain and model strain cultivation. HIV1-protease band is located at 11 kDa.

Figure 12:
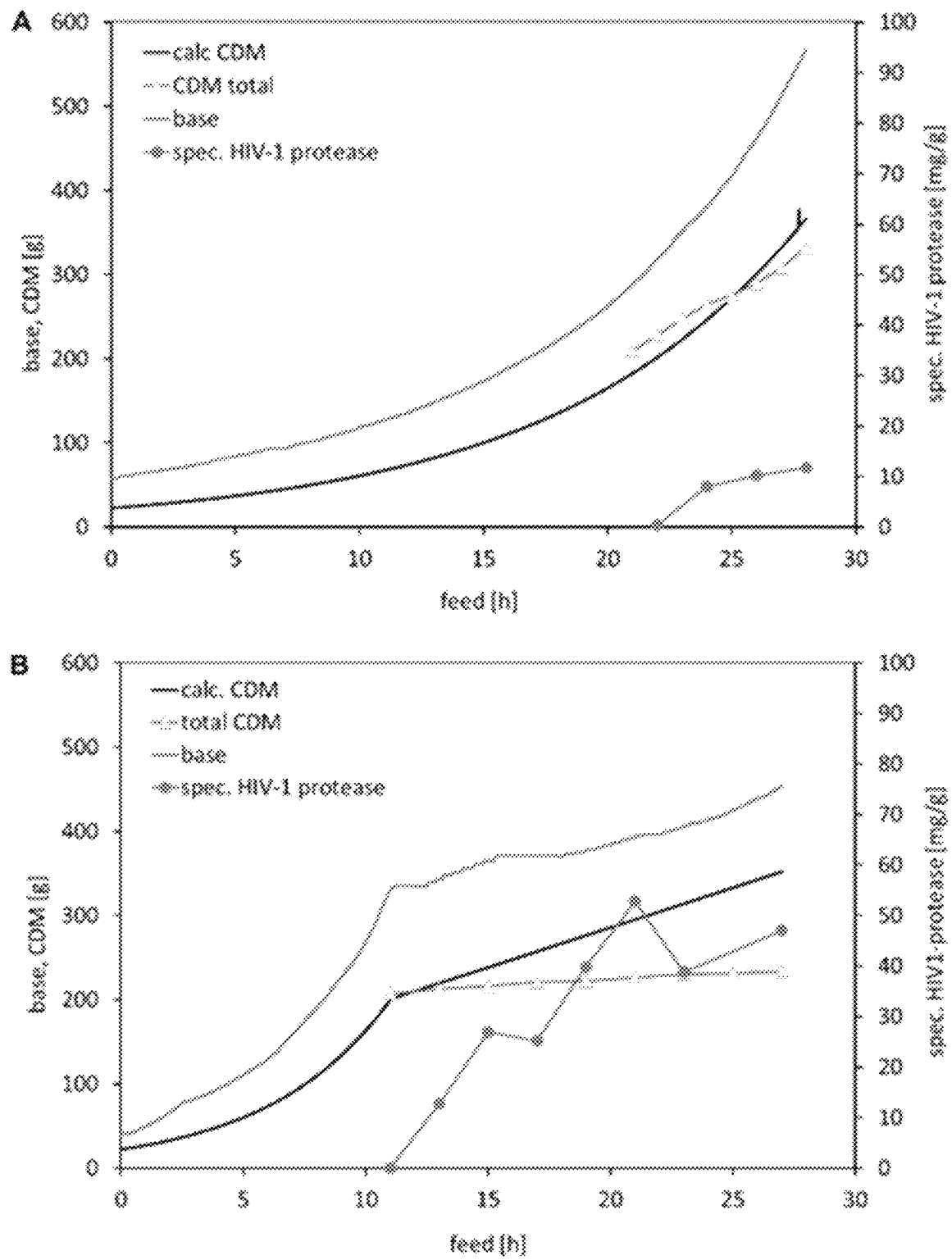

FIG. 12: Growth and product formation kinetics of strain BL21(DE3)pET30a(HIV1-protease) and BL21(DE3): TN7<GP2ΔAra>pET30a(HIV1-protease).

Figure 13:
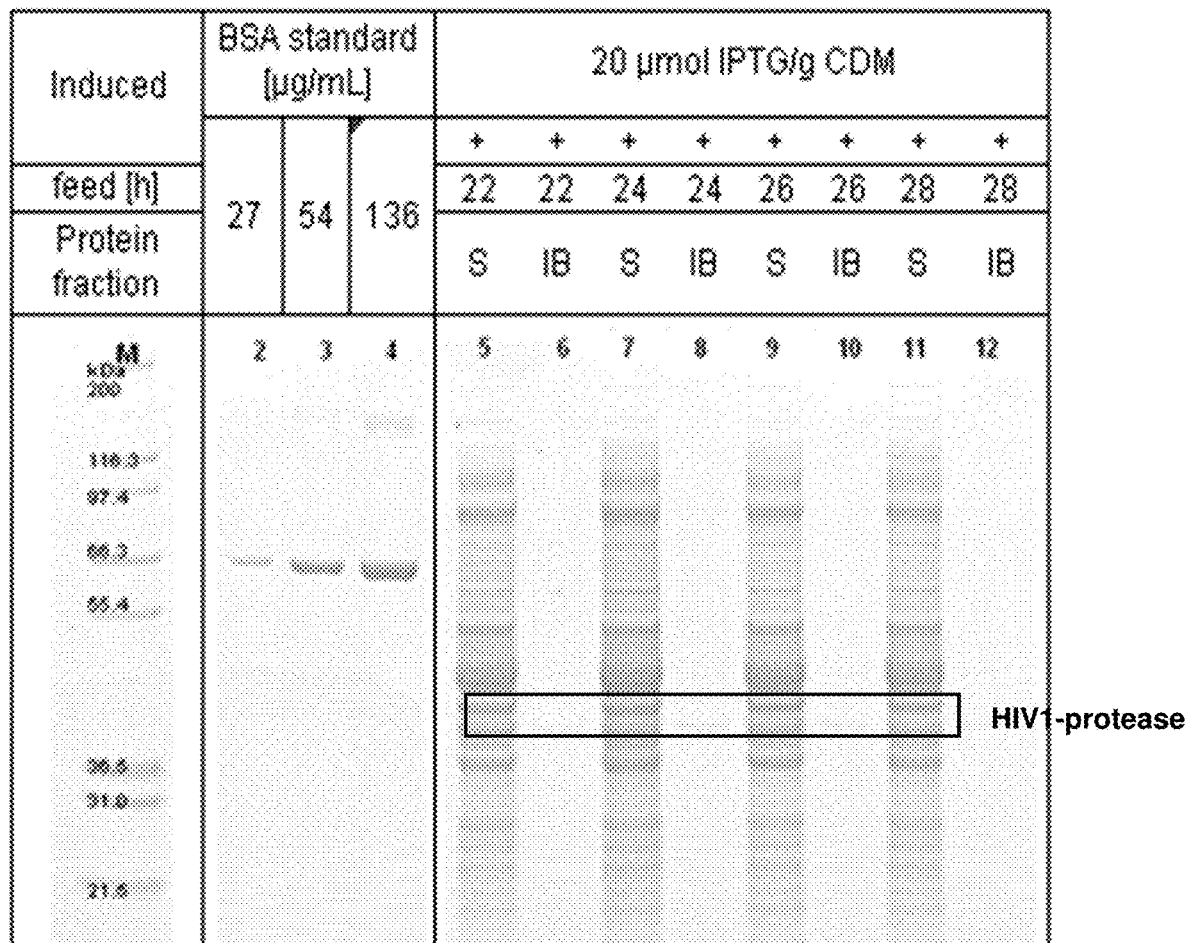

(A) Reference fermentation process: Induction with 20 μmol IPTG/g CDM at feed 21 h with exponential feed rate of μ=0.10 h$^{-1}$; (B) Model fermentation process: Induction with 0.1 M arabinose+20 μmol IPTG/g at feed 11 h where exponential feed (μ=0.20 h$^{-1}$) was switched to linear feed;

FIG. 13: SDS page analysis of reference process fermentation with BL21(DE3)pET30(HIV1-protease).

Figure 14:
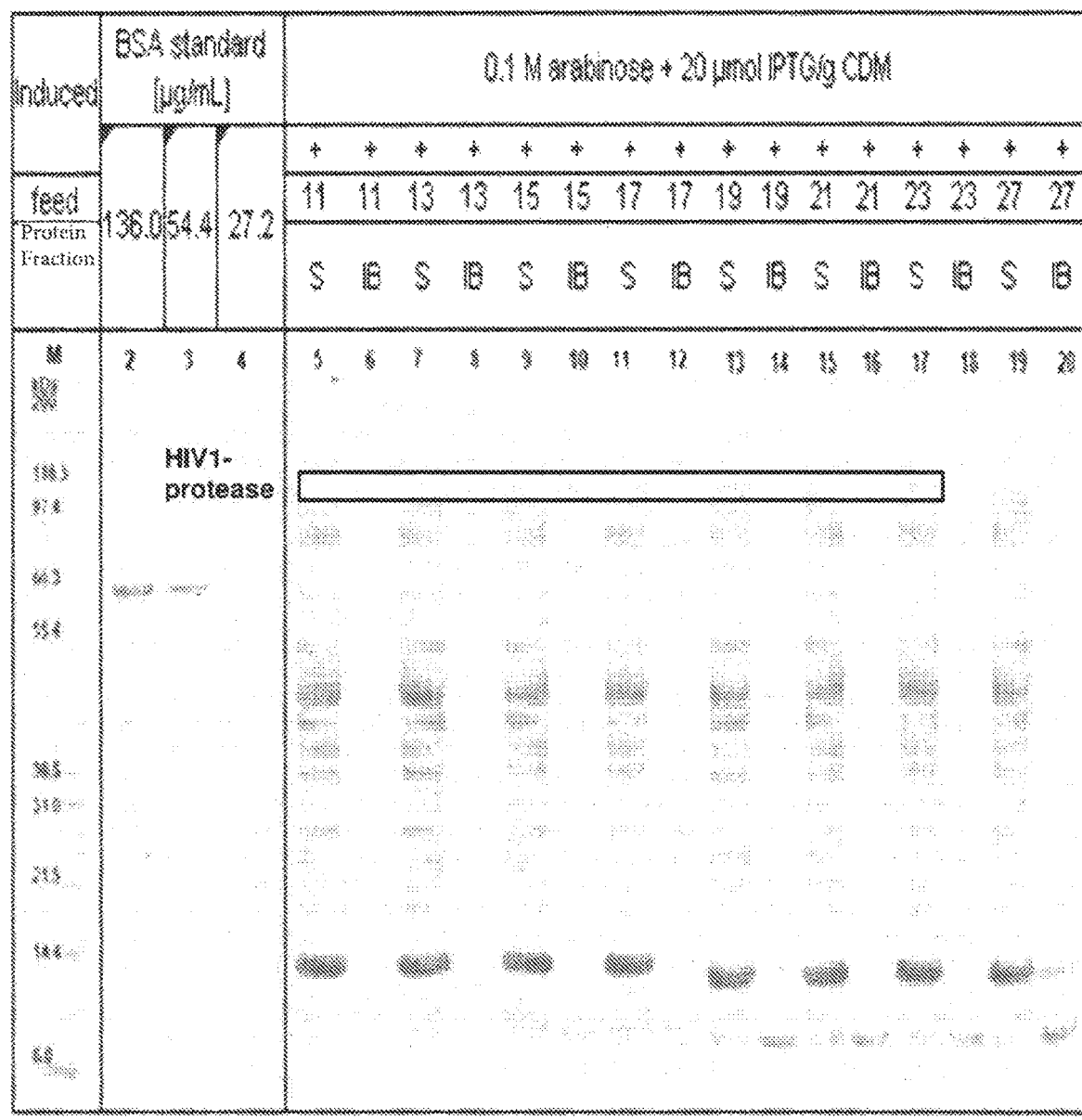

FIG. 14: SDS PAGE analysis: Cultivation of BL21 (DE3)::TN7(Gp2ΔAra)pET30(HIV1-protease).

Figure 15:
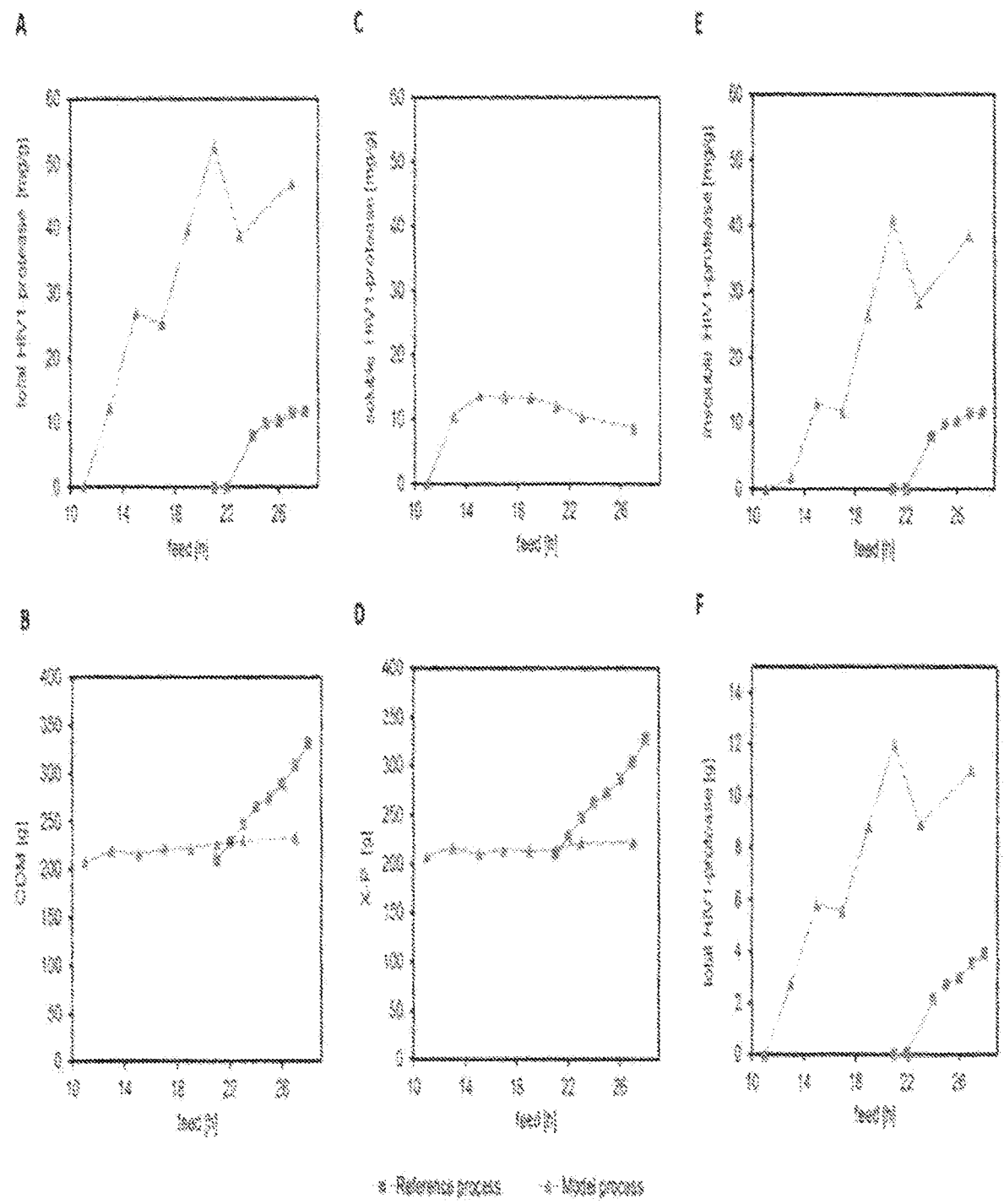

FIG. 15: Comparison of HIV1-protease production yields by BL21(DE3)::TN7(Gp2ΔAra)pET30(HIV1-protease) [model process, green] and BL21(DE3)pET30a(HIV1-protease) [reference process, red].

(A, C, E) Comparison of produced total, soluble and insoluble HIV1-protease; (B, D) Comparision of total CDM and net CDM; (F) Total HIV1-protease produced by both systems.

Figure 16:
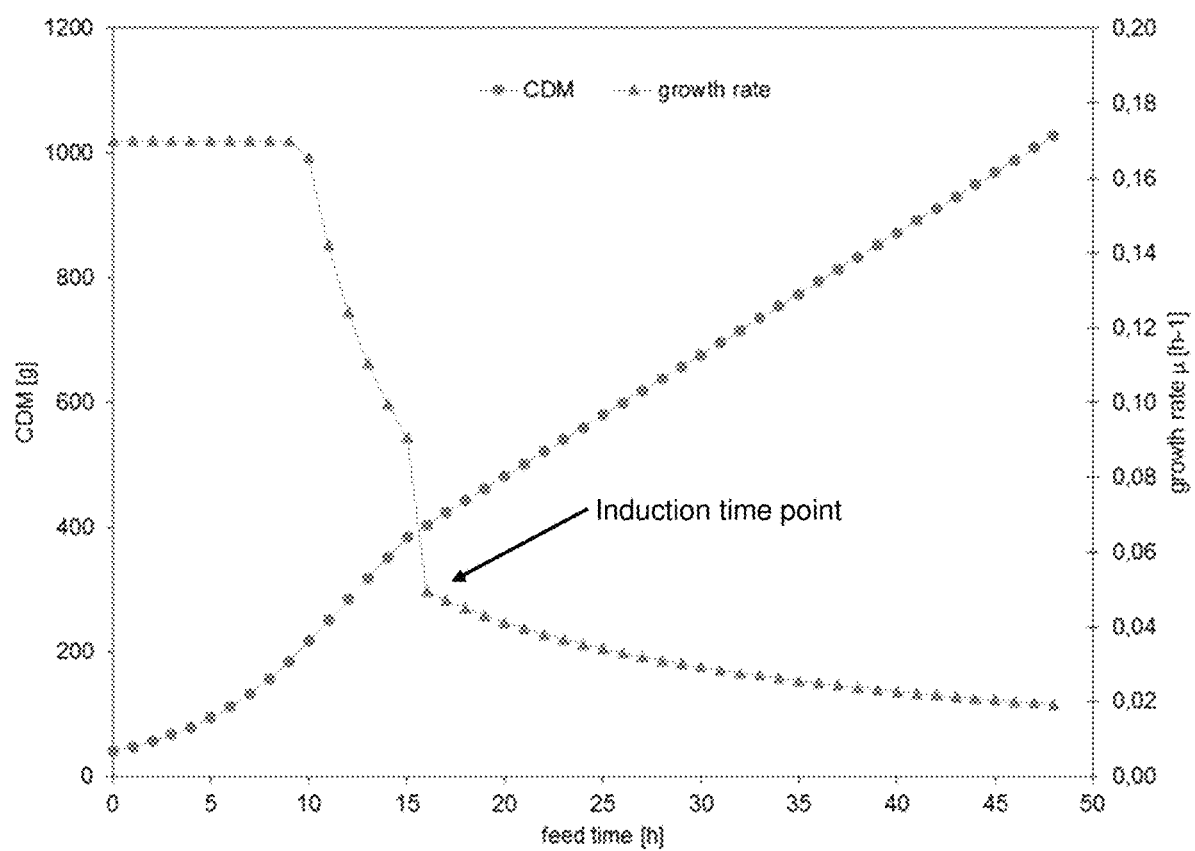

FIG. 16: Established feed profile for growth decoupled protein expression in HCD bioreactor fed-batch cultivation.

Theoretical trends of growth curve and growth rate, calculation based on a constant glucose yield coefficient throughout the cultivation.

Figure 17:
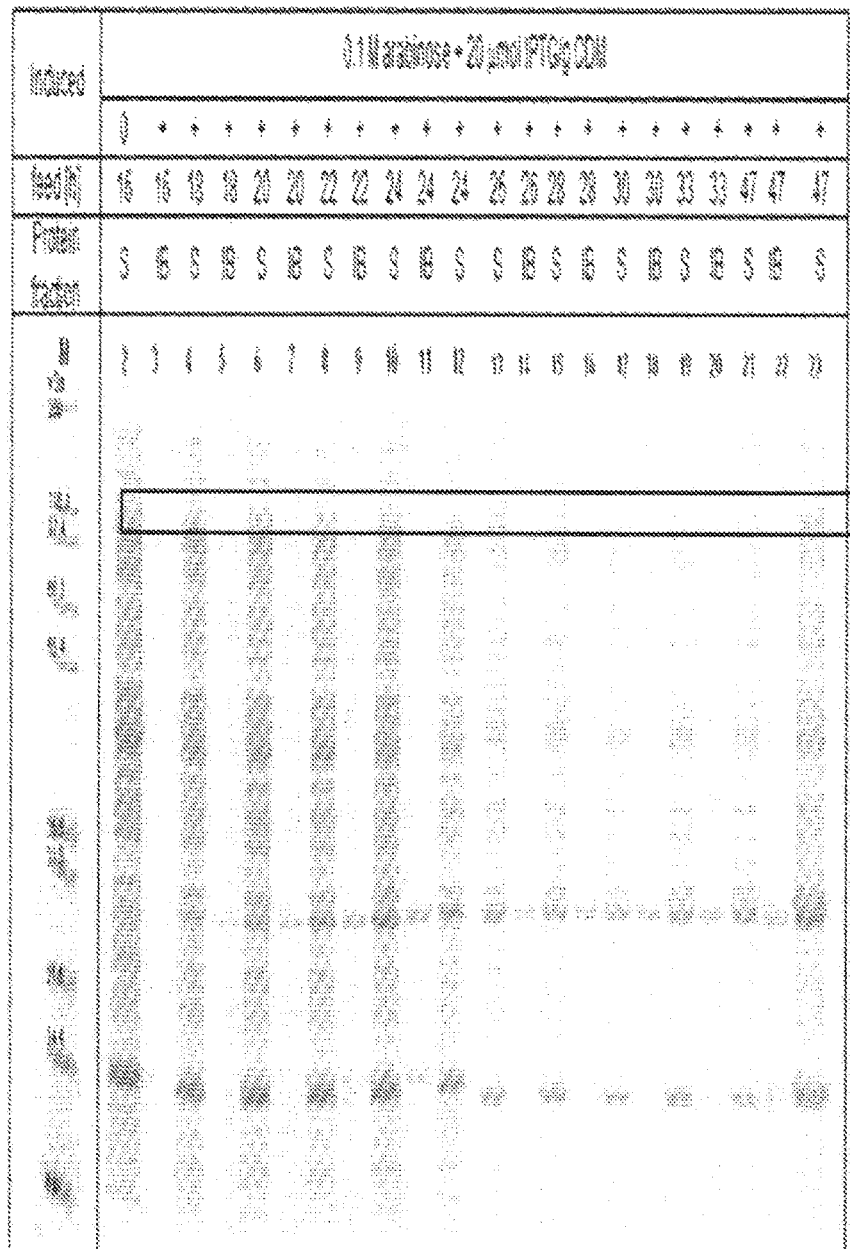

FIG. 17: SDS page analysis of HCD cultivation of. BL21(DE3)::TN7(Gp2ΔAra)pET30(GFPmut3.1).

Induced with 20 μmol IPTG/g CDM and 0.1 M arabinose at feed hour 15 where exponential feed ($\mu$=0.17 h$^{-1}$) was switched to linear feed. GFP band is located at 27 kDa.

Figure 18:
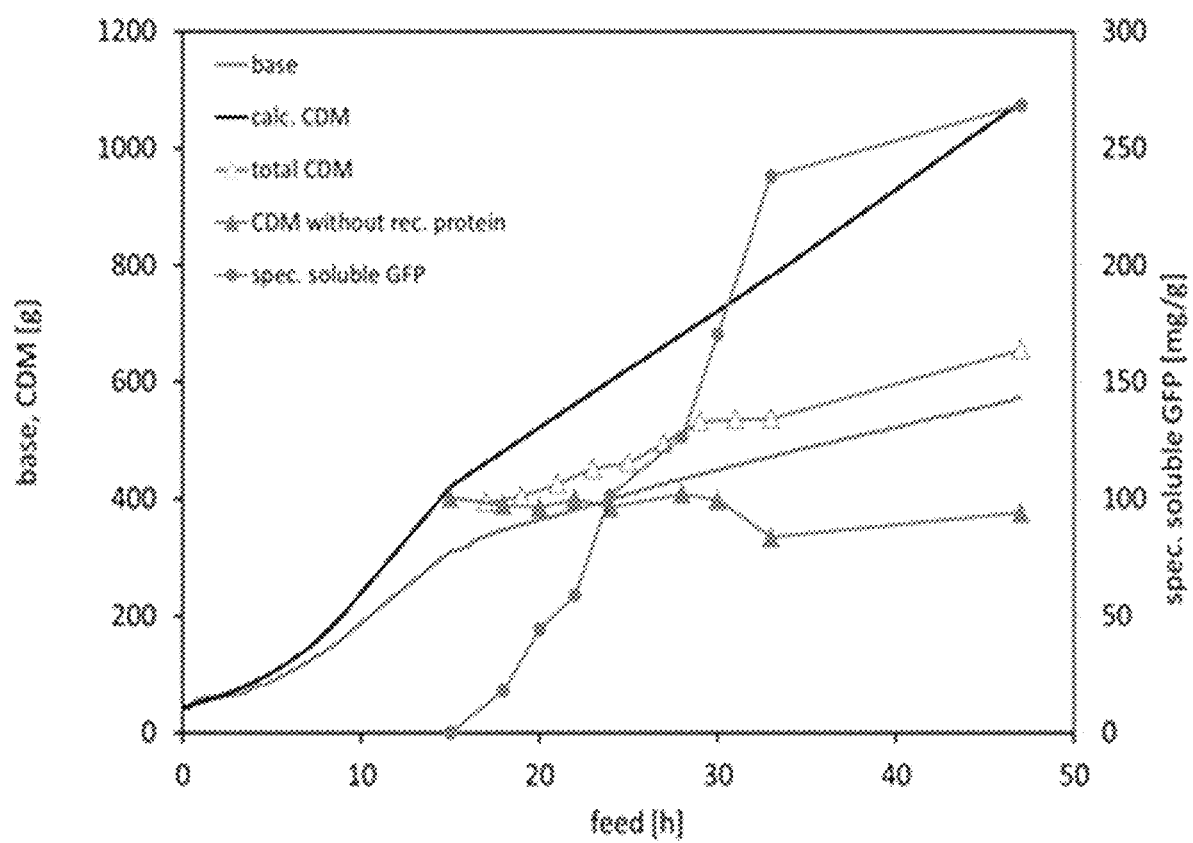

FIG. 18: Growth and product formation kinetics of HCD cultivation of strain BL21(DE3):TN7<GP2ΔAra>pET30a (GFPmut3.1).

Induction with 0.1 M arabinose+20 μmol IPTG/g at feed 15 h where exp. feed ($\mu$=0.20 h$^{-1}$) was switched to linear feed.

Figure 19:
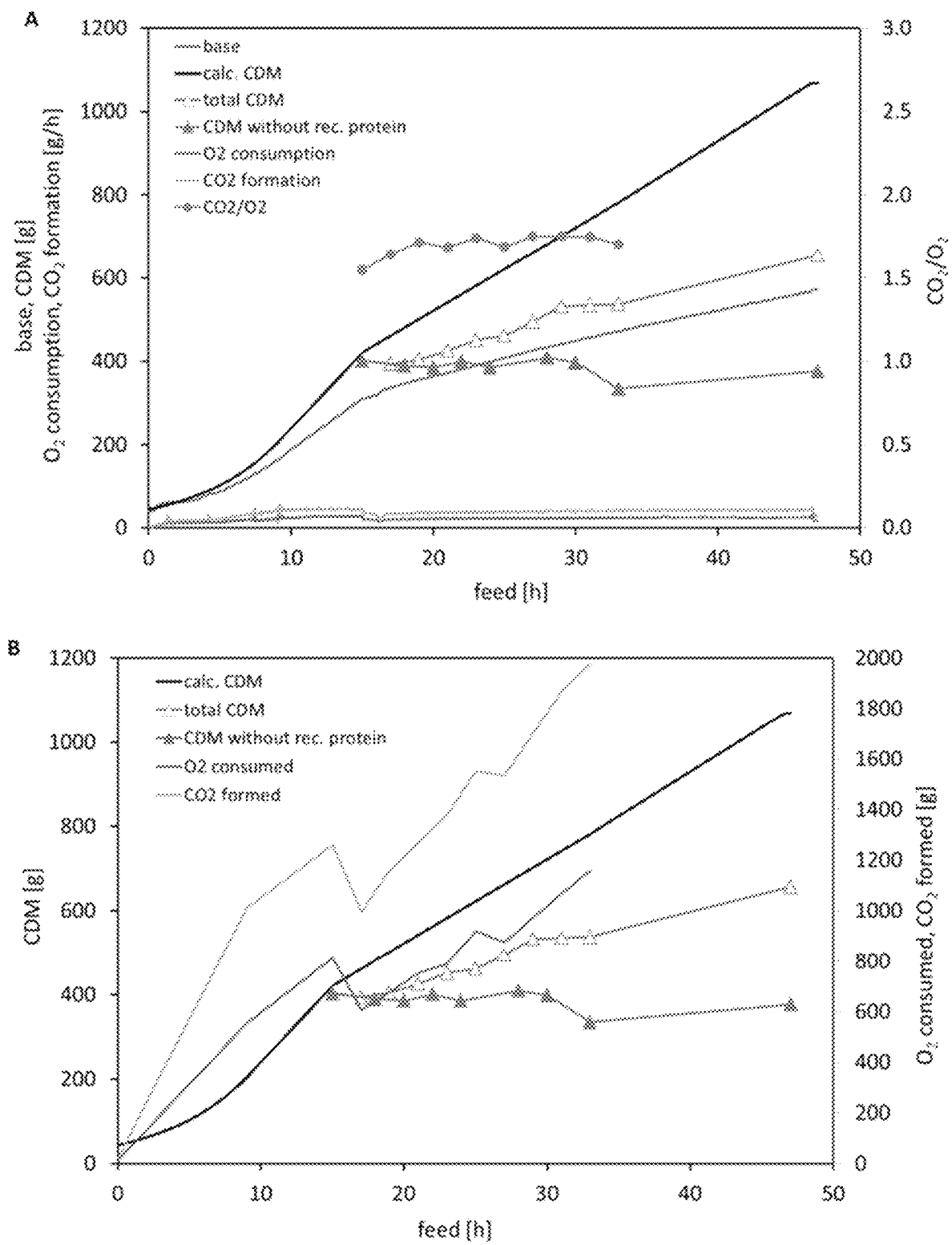

FIG. 19: Hourly (A) and total (B) $O_2$ consumption and $CO_2$ formation during HCD cultivation of growth decoupled system.

Induction with 0.1 M arabinose+20 μmol IPTG/g CDM at feed 15 h with exponential feed rate of $\mu$=0.17 h$^{-1}$; Feed medium supplemented with $(NH_4)_2SO_4$.

Figure 20:
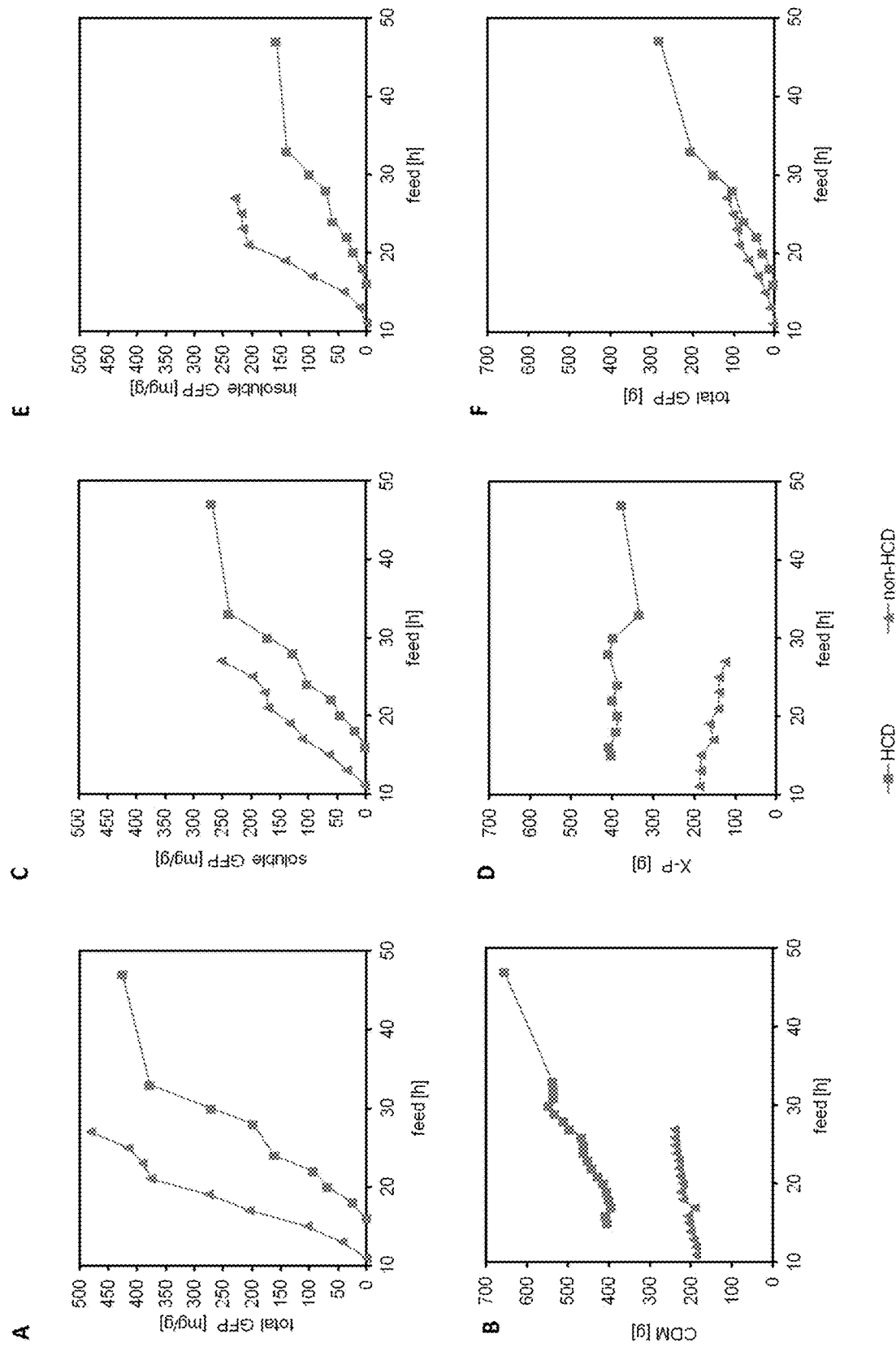

FIG. 20: Comparison of GFPmut3.1 production yields between HCD and non-HCD cultivation of BL21(DE3):: TN7(Gp2ΔAra)pET30(GFPmut3.1).

(A, C, E) Comparison of produced total, soluble and insoluble GFPmut3.1; (B, D) Comparison of total CDM and net CDM; (F) Total GFPmut3.1 produced.

EXAMPLES

The following Examples illustrate the invention, but are not to be construed as limiting the scope of the invention.

Example 1: Inhibition of the Host Cells RNA Polymerase Inhibits Growth of the Host Cell In order to assess the effect of inhibition of the host cells RNA polymerase on proliferation of the host cell the Gp2 encoding sequence under control of an arabinose-inducible promoter was cloned in the low-copy f-plasmid pKLJ12 (Jones and Keasling (1998) Biotechnol Bioeng Vol. 59, Issue 6: 659-665), which constitutes only a small burden to the host cell and is stably maintained. The protein Gp2 is known to inhibit the host cell RNA polymerase by binding to the beta-subunit of the enzyme. The plasmid pKLJ12+Gp2 was transformed in E. coli strain NEB10-beta which comprises an araD139 mutation. Consequently, NEB10-beta is not capable of metabolizing the inducer arabinose. At the time point 0 h several cultures were inoculated and Gp2 expression was induced after 2 h by addition of 1.5%, 0.1% or 0.001% arabinose. Proliferation of the bacteria was measured by determining the OD600 nm value. Addition of different concentrations of arabinose and thereby expression of Gp2 caused an inhibition of proliferation in a dose-dependent manner in comparison to a bacteria culture where arabinose has been omitted (FIG. 1). In order to exclude any effect of the compound arabinose on host cell growth a derivative of plasmid pKLJ12+Gp2 lacking the ribosome binding site of the Gp2 expression cassette has been employed. Consequently, expression of Gp2 cannot be induced and hence no difference in proliferation was observed with or without arabinose (FIG. 2).

Example 2: Integration of the Gp2 Encoding Expression Cassette in the Host Cells Genome In order to confer a stable expression of the Gp2 protein in the host cell population the Gp2 encoding expression cassette was integrated in the genome of NEB10-beta via homologous recombination at the TN7 locus. The inserted sequence comprised the Gp2 gene under control of an arabinose promoter, a regulator, a terminator, and an ampicillin resistance gene. To this end, a 50 bp overhang was added to the insertion element via PCR. The linear PCR product was concomitantly transformed into the NEB10-beta host cell with a pSIM helper plasmid, which confers heat shock induced expression of proteins mediating the integration of the PCR product in the host cells genome. After successful integration the pSIM plasmid can be withdrawn from the host cell (Sharan et al., 2009, Nat Protoc. 4(2):206-23).

Example 3: Induced Expression of Gp2 in E. coli Increases the Expression of the Model Protein GFP E. coli strain HMS174(DE3) TN7::<T7GFP>, comprising the GFP encoding sequence under control of a T7 promoter and T7 RNA polymerase under control of an IPTG-inducible promoter, was transformed with the plasmid pKLJ12+Gp2 which harbours the Gp2 encoding sequence under control of an arabinose-inducible promoter. About 2 h after inoculation of the culture IPTG was added to induce the expression of T7 RNA polymerase and thereby GFP. About 3 h after inoculation arabinose was added in order to express Gp2. Three consecutive experiments showed that host cells induced with IPTG and arabinose, expressing T7 RNA polymerase and Gp2, expressed GFP to a higher extent compared to host cells that were induced with IPTG, only, and therefore expressed T7 RNA polymerase but not Gp2. In the two samples lacking IPTG with or without arabinose GFP was slightly expressed due to leakiness of the promoter (FIG. 3).

Example 4: Expression of Gp2 from the pKLJ12+Gp2 Insert without the Vector Increases the GFP Expression E. coli strain HMS174(DE3) TN7::<T7GFP>, comprising the GFP encoding sequence under control of a T7 promoter and T7 RNA polymerase under control of an IPTG-inducible promoter, was transformed with the insert of pKLJ12+Gp2 comprising the Gp2 expression cassette. In two out of three cases the transformation of the Gp2 expression cassette resulted in an increased GFP expression 3 h after IPTG induction (FIG. 4).

Example 5: Description of an Example Fermentation Process in which the Effect of Gp2 Expression on the Yield of the Model Protein GFP was Assessed Cultivation Mode and Process Analysis The cells are grown in a 12 L (8 L net volume, 4 L batch volume) computer-controlled bioreactor (MBR; Wetzikon, CH) equipped with standard control units. The pH is maintained at a set-point of 7.0±0.05 by addition of 25% ammonia solution (ACROS Organics), the temperature is set to 37° C.±0.5° C. In order to avoid oxygen limitation, the dissolved oxygen level is stabilized above 30% saturation by stirrer speed and aeration rate control. Fluorescence measurements are performed using a multi-wavelength spectrofluorometer specially designed for online measurements in an industrial environment, the BioView® (DELTA Light & Optics, Lyngby, Denmark). Foaming is suppressed by addition of antifoam suspension (PBG2000) with a concentration of 0.5 ml/l medium. For inoculation, a deep frozen (−80° C.) working cell bank vial, is thawed and 1 ml (optical density $OD_{600}=1$) is transferred aseptically to the bioreactor. Feeding is started when the culture, grown to a bacterial dry matter of 22.5 g in 4 L batch medium, entered stationary phase. With start of the feed phase cultivation temperature is reduced to 30° C. The feed medium provided sufficient components to yield another 363 g of bacterial dry matter (4 doublings).

In the reference process (FIG. 6) the (standard) expression system *E. coli* BL21(DE3)pET30a GFPmut3.1 was used. The growth rate in the feed phase was set to 0.1 $h^{-1}$ and 3 doublings past feed start induction of recombinant gene expression was conducted with 20 µmol IPTG per gram CDM by a single pulse directly to the bioreactor.

In the process with the (standard) expression system *E. coli* BL21(DE3)pET30a GFPmut3.1 containing a genome integrated inducible Gp2 protein (FIG. 7) the growth rate in the feed phase was set to 0.2 $h^{-1}$ for 3 doublings via an exponential substrate feed. Afterwards induction with 20 µmol IPTG per gram cell dry mass and 10 mmol arabinose is conducted and the medium feed is switched to a linear feed for another 16 h with an initial growth rate of 0.05 $h^{-1}$. The substrate feed is controlled by increasing the pump speed according to the exponential growth algorithm, $x=x_0 \cdot e^{\mu t}$, with superimposed feedback control of weight loss in the substrate tank.

Media Composition

The minimal medium used in this study contains 3 g $KH_2PO4$ and 6 g $K_2HPO4 \ast 3H_2O$ per litre. These concentrations provide the required buffer capacity and serve as P and K source as well. The other components are added in relation of gram bacterial dry matter to be produced: sodium citrate (trisodium salt $\ast 2H_2O$; ACROS organics) 0.25 g, $MgSO_4 \ast 7H_2O$ 0.10 g, $CaCl_2 \ast 2H_2O$ 0.02 g, trace element solution 50 µl and glucose$\ast H_2O$ 3 g. To accelerate initial growth of the population, the complex component yeast extract 0.15 g is added to the minimal medium to obtain the batch medium. For the feeding phase 8 L of minimal medium are prepared according to the amount of biological dry matter 363 g to be produced in the feeding phase, whereby P-salts are again added per litre. Trace element solution: prepared in 5 N HCl (g/L): $FeSO_4 \ast 7H_2O$ 40.0, $MnSO_4 \ast H_2O$ 10.0, $AlCl_3 \ast 6H_2O$ 10.0, $CoCl_2$ (Fluka) 4.0, $ZnSO_4 \ast 7H_2O$ 2.0, $Na_2MoO_2 \ast 2H_2O$ 2.0, $CuCl_2 \ast 2H_2O$ 1.0, $H_3BO_3$ 0.50.

Offline Analysis

Optical density (OD) is measured at 600 nm. Bacterial dry matter is determined by centrifugation of 10 ml of the cell suspension, re-suspension in distilled water followed by centrifugation, and re-suspension for transfer to a pre-weighed beaker, which is then dried at 105° C. for 24 h and re-weighed. The progress of bacterial growth is determined by calculating the total amount of cell dry mass (total CDM).

The content of recombinant protein GFP is determined by ELISA and electrophoretic protein quantification using densitometric quantification of bands on an SDS-PAGE gel. Soluble recombinant product is quantified via GFP-ELISA, while the recombinant product in the inclusion bodies is determined with SDS-PAGE gel electrophoresis.

Additionally, supernatant and inclusion bodies were analysed using SDS-PAGE gel electrophoresis. The coomassie stained SDS PAGE gel shows an increase of soluble GFP in the supernatant using the growth decoupled system compared to a standard system. Furthermore, the relative amount of GFP to HCP in the supernatant is considerably higher using the growth decoupled system compared to a standard system. Additionally, solubility of GFP is improved by using the growth decoupled system compared to a standard system (BL21(DE3)pET30a GFPmut3.1) which is not growth decoupled (FIG. 8).

Example 6: Production of HIV-1 Protease Using the Growth Decoupled System

To prove the applicability of the developed growth decoupled process, alternative recombinant proteins were required. For that purpose HIV-1 protease was selected as second model protein for verification of the growth decoupled system and the model process, as it is difficult to produce because it is highly toxic for *E. coli* (Korant and Rizzo, (1991), Biomed Biochim Acta 50: 643-6). Overexpression of this aspartic protease from the human immunodeficiency virus type 1 in *E. coli* is usually accompanied by toxic effects on the producing cells (Fernandez et al., (2007), Biotechnol Lett 29: 1381-6), possibly linked to its proteolytic activity. Consequently, this protein is generally difficult to express in microbial systems. The retroviral proteins are synthesized as polyprotein precursors and are processed by specific proteases (Volonté et al., (2011), Microb Cell Fact 10: 53). These precursors are Gag and Gag-Pol polypeptides, which are proteolytically processed by HIV-1 protease to mature proteins (Kohl et al., (1988), Proc Natl Acad Sci USA 85: 4686-90).

HIV-1 protease is encoded by HI-virus and thereby plays an important role in the maturation of the virus. It is an appealing target for development of a possible treatment of the acquired immune deficiency syndrome (AIDS). The availability of a system which can express large amounts of HIV-1 protease in bacterial cultivation systems is the ultimate goal of obtaining large quantities of this protein. (Volonté et al., (2011), Microb Cell Fact 10: 53)

Reference Fermentation Process:

The batch phase of the cultivation was performed at a temperature of 37° C. and was inoculated with 1 mL of working cell bank (WCB). Depending on the experiment, following strains, containing two different model proteins, were used for this process scheme:

BL21(DE3)pET30(GFPmut3.1)
BL21(DE3)pET30(HIV1-protease)

The batch phase was completed after 11 h to 13 h (indicated by a peak in dissolved oxygen) and the feed phase was started immediately afterwards. In the exponential feed phase the temperature was decreased to 30° C. in order to reduce inclusion body formation of the expressed recombinant protein as well as to achieve better 02-solubility. The growth rate (µ) of the fed batch process was kept constant at 0.10 $h^{-1}$ by an exponential substrate feed for 4 generations. Feeding was initiated after the cell dry mass (CDM) reached the end of the batch phase with 22.5 g CDM in 4 L batch volume.

Induction with a single pulse of IPTG (20 µmol/g CDM) took place after the $3^{rd}$ generation (21 h after feed start) in the feed-phase. The sampling procedure lasted for 1 generation. An overview on the reference process scheme is shown in FIG. 9.

Fermentation Process/Growth Decoupled Production System:

The batch phase of the cultivation was performed at a constant temperature of 37° C. and was inoculated with 1 mL of WCB. The following systems were cultivated with this process scheme:

BL21(DE3)::TN7(Gp2ΔAra)pET30(GFPmut3.1)
BL21(DE3)::TN7(Gp2ΔAra)pET30(HIV1-protease)

The batch-phase completed after 11 h to 13 h and the feed phase was started immediately afterwards. In the exponential feed phase the temperature was decreased to 30° C. in order to achieve a better solubility of the expressed recombinant protein and to reach a better oxygen transfer rate (OTR). The growth rate was kept constant at $\mu=0.20\ h^{-1}$. The recombinant protein production was induced with a single pulse of 0.1 M arabinose (Gp2) and 20 µmol IPTG/g CDM (gene of interest—GOI) after the 3rd generation (21 h after feed start). During the 4th generation sampling took place, a linear feed profile was applied starting with an initial growth rate of $\mu=0.050\ h^{-1}$ that decreased to $\mu=0.025\ h^{-1}$ in the course of the experiment. The sampling procedure lasted for 1 generation. An overview on the reference process scheme is shown in FIG. 10.

HIV-1 Protease Production in *Escherichia coli*:

In order to prove broad applicability of the platform process, experiments with alternative recombinant proteins are required. For that purpose HIV-1 protease, a protein difficult to be produced in *E. coli*, was selected for benchmarking experiments.

Before bioreactor cultivations of the reference strain BL21(DE3)pET30a(HIV1-protease) and the model strain BL21(DE3)::TN7(Gp2ΔAra)pET30(HIV1-protease) were carried out, standard shake flask cultivations were performed for verification if the recombinant protein is produced. HIV-protease band is located at 11 kDa under the lysozyme band. Following linear equation was used for quantification of HIV1-protease:

$$y=0.0007x\ R^2=0.9708$$

According FIG. 11, both strains were able to produce HIV1-protease in insoluble form. Production of the growth decoupled system yielded a concentration of 69 µg/mL, while the reference system produced only 5 µg/mL insoluble HIV1-protease. Consequently BL21(DE3)::TN7(Gp2ΔAra)pET30(HIV1-protease) was able to produce 13 times more HIV1-protease than the reference strain.

As both strains were capable of producing the model protein, lab scale cultivations of both systems were performed. BL21(DE3)pET30a(HIV1-protease) was used as reference system and the fermentation process was performed according to the description above. In parallel the new platform process with the growth decoupled system was performed as described in FIG. 10 with BL21(DE3)::TN7 (Gp2ΔAra)pET30(HIV1-protease). A growth rate of $\mu=0.20\ h^{-1}$ was applied during the exponential feed phase.

As shown in graph A of FIG. 12, the maximal specific concentration of HIV-1 protease for the standard process was 11.8 mg/g CDM with no soluble expression of the protein. The obtained volumetric yield with 0.3 g/L is also very low. This result confirms the statement that HIV-1 protease belongs to the group of low yield and difficult-to-express proteins (Volonté et al., (2011), Microb Cell Fact 10: 53; Wörsdörfer et al., (2011), Science 331: 589-92). Graph B shows that in the model process, the growth of CDM stopped after induction and there was no decrease in net CDM. At the end of the process the growth decoupled system produced 233.5 g CDM in total. Compared to the reference process, which produced 331.92 g CDM, the model process generated 30% less CDM. After induction of the protein production, the model process also consumed 155.2 g less base compared to the reference system. FIG. 13 shows SDS page analysis of the reference process. Following linear equation was used for quantification of the reference process fermentation:

$$y=0.0006x\ R^2=0.9981$$

According to FIG. 13, the reference system was only capable of producing HIV1-protease in insoluble form (IB). At the beginning of the protein expression phase, BL21 (DE3)pET30(HIV1-protease) produced 2 µg insoluble HIV1-protease per mL. At the end of the 4$^{th}$ generation the reference process yielded 19 µg insoluble HIV1-protease per mL.

FIG. 14 displays SDS page analysis of the growth decoupled process fermentation. Following linear equation was used for quantification of HIV1-protease:

$$y=0.0009x\ R^2=0.9611$$

According to FIG. 14, the growth decoupled system was capable of producing HIV1-protease in soluble (S) and insoluble form (IB). At the beginning of the protein production phase BL21(DE3)::TN7(Gp2ΔAra)pET30(HIV1-protease) expressed 79% soluble and 21% insoluble HIV1-protease. The ratio of soluble protein decreased with prolonged process duration. At the end of the 4$^{th}$ generation (27 h after feed start) 12% were expressed as soluble and 88% as insoluble HIV1-protease.

A summary of results of these experiments is shown in FIG. 15. As displayed in graph A, the growth decoupled system was capable of producing HIV1-protease with a concentration of 47 mg/g CDM, whereas the reference process produced a total HIV1-protease concentration of 12 mg/g CDM. Thus, BL21(DE3)::TN7(Gp2ΔAra)pET30 (HIV1-protease) produced almost four times more HIV1-protease per gram CDM compared to BL21(DE3)pET30a (HIV1-protease). According to graph C, the model process yielded a concentration of 9 mg/g soluble HIV1-protease at the end of the process while the reference strain was not able to produce HIV1-protease in soluble form. As seen in graph F, the model process produced a total mass of 11 g HIV1-protease, whereas the reference process only reached a total output of 4 g. In conclusion the model process produced about three times more HIV1-protease compared to the reference process. Graph D of FIG. 15 shows the calculated net CDM without produced recombinant product (X-P) in gram. X-P remained constant compared to the total CDM production (graph B). After induction of the growth decoupled system 26 g of CDM where built until the end of the process, whereas the reference system produced 122 g CDM during the production phase. In summary, the growth decoupled system produced 282% more HIV1-protease with about 30% less CDM compared to the reference system.

Example 7: High-Cell-Density Cultivations (HCDC) Using the Growth Decoupled System The results from the non-HCD bioreactor cultivations indicated that the growth decoupled expression system should allow variable growth rates before induction which is important for HCD cultivations as a growth rate of $\mu=0.2\ h^{-1}$ is hard to maintain without the risk of oxygen limitation. A too high growth rate would result in suboptimal conditions, especially during the exponential feed phase. The HCD process was planned to reach a CDM concentration of 60 g/L at induction time point. As the performed HCDC should only show the ability of the growth decoupled system to reach comparable specific amounts of protein and higher productivity in a semi-HCDC compared to non-HCDC, GFPmut3.1 was used as only model protein. The HCD fermentation plan is shown in FIG. 16. The batch was performed at a temperature of 37° C. and completed after 16 h. An exponential feeding phase ($\mu=0.17\ h^{-1}$) was started immediately after the batch phase finished, which lasted for about 2 generations. The feed medium was also supplemented with ammonium sulphate to guarantee non-nitrogen-limiting conditions. Afterwards the first linear feed profile was applied which lasted for 1 generation. 15 h after start of the feeding phase the protein production was induced with 0.1 M arabinose+20 μmol IPTG/g CDM. During the production phase a second linear feed profile was applied, which lasted for about 1 generation with a decreased calculated growth rate starting from $\mu=0.050\ h^{-1}$ at the beginning to a $\mu$ of $0.020\ h^{-1}$ at the end of the process. The protein expression phase lasted for 33 h. The purpose of the resulting low growth rate was to supply just enough glucose to the strain as it needed to express the POI.

FIG. 17 shows SDS page analysis of the HCD cultivation of the growth decoupled system. After 33 h of protein production BL21(DE3)::TN7(Gp2ΔAra)pET30 (GFPmut3.1) was capable of producing 63% soluble and 37% insoluble GFP, which is an improvement compared to the non-HCD cultivation of the growth decoupled system process and shows that upscaling to HCDC has no significant impact on the solubility of the expressed protein.

FIG. 18 shows the results of the HCDC of the growth decoupled system. BL21(DE3)::TN7(Gp2ΔAra)pET30 (GFPmut3.1) was capable of producing 268.4 mg soluble and 157.6 mg insoluble GFP per g CDM. During the production phase a total amount of 279.5 g GFP has been produced and 176.1 g thereof in soluble form. The process yielded a concentration of 30 g/L GFP which is an increase of 300% compared to the non-HCD of the growth decoupled system. After induction of protein expression the net CDM stopped and remained more or less constant, which agrees with the results from the non-HCDC of the growth decoupled system.

Analysis of total $O_2$ consumption and total $CO_2$ formation during protein production of the HCD model fermentation process showed that the growth decoupled system forms a comparable high amount of total $CO_2$ as the non-HCDC of the growth decoupled system. As seen in graph A of FIG. 19, after induction of protein production $O_2$ consumption and $CO_2$ formation of BL21(DE3)::TN7(Gp2ΔAra)pET30 (GFPmut3.1) remained constant, which shows that the HCD process is still metabolically active.

FIG. 20 shows a summary of results between the HCD and the non-HCD cultivation of the growth decoupled system. Graph A shows that non-HCDC of BL21(DE3):: TN7(Gp2ΔAra)pET30(GFPmut3.1) was capable of producing 480.18 mg GFP per g CDM, which is the highest specific concentration of all performed cultivations. The HCD process reached a comparable high specific concentration with 426 mg GFP per g CDM. Furthermore the HCDC process was capable of producing 7% more specific GFP in soluble form. As seen in graph D, during both cultivations the growth of net CDM stopped and decreased after induction of the protein expression. At the time of induction the HCDC process reached a CDM concentration of 57 g/L and generated 216% more gross CDM compared to the non-HCDC process, which reached 22 g/L at the time of induction (graph B). HCDC of the growth decoupled system produced a total amount of 280 g GFP which is an increase of 243% compared to non-HCDC of the system (graph F). In consideration of the total produced CDM, shown in graph B and the produced net CDM, shown in graph F, the HCDC produced 243% more GFP with 300% more net CDM compared to the non-HCDC. Graph D displays the calculated net CDM without produced recombinant protein (X-P) in g. The decrease of net CDM proved that after induction of both system almost exclusively recombinant GFPmut3.1 is produced.

Comparison of the total produced GFP and the produced net CDM between the non-HCD and the HCD process shows that the growth decoupled system shows a linear relationship between the produced GFP and the net CDM even in the up-scaled HCD process. It also reveals that HCD cultivation of the growth decoupled system has high potential for further HCDC fermentation with much higher CDM concentrations. Cultivation with a CDM concentration up to 100 g/L prior induction should yield an enormous amount of GFP.

---

The invention claimed is:

1. A bacterial host cell which is *E. coli* and which
   (i) comprises under the control of an inducible promoter a nucleotide sequence encoding a phage protein which inhibits growth of said bacterial host cell; and
   (ii) comprises a nucleotide sequence encoding a RNA polymerase which is heterologous for said bacterial host cell, wherein sail RNA polymerase, which is heterologous for said bacterial host cell is bacteriophage T3 RNA polymerase, T7 bacteriophage RNA polymerase, engineered orthogonal TI RNA polymerase, bacteriophage SP6 RNA polymerase or bacteriophage Xp10 RNA polymerase; and
   (iii) comprises a nucleotide sequence which encodes a protein of interest under the control of a promoter recognized by said RNA polymerase, which is heterologous for said host cell;
   wherein said nucleotide sequence encoding a phage protein which inhibits growth of said bacterial host cell and sail nucleotide sequence encoding said RNA polymerase, which is heterologous for said bacterial host cell are integrated into the genome of said host cell,
   wherein said phage protein which inhibits growth of said bacterial host cell is
   (a) a protein having the amino acid sequence shown in Seq Id No: 1 which inhibits bacterial host cell RNA polymerase; or
   (b) a protein having an amino acid sequence which has an identity of 80% or more to the full-length of the amino acid sequence shown in Seq Id No: 1 and which inhibits bacterial host cell RNA polymerase.

2. The bacterial host cell of claim 1, wherein said nucleotide sequence encoding a protein of interest is comprised by an extrachromosomal vector.

3. The bacterial host cell of claim 1, wherein said nucleotide sequence encoding said RNA polymerase, which is heterologous for said bacterial host cell, is under the control of an inducible promoter.

4. The bacterial host cell of claim 3, wherein said inducible promoter is regulated by arabinose, IPTG, tryptophane, xylose, rhamnose, phosphate or phage lambda cI protein.

5. The bacterial host cell of claim 1, wherein said host cell has a non-functional arabinose operon.

6. A preparation of a bacterial host cell which is *E. coli* and which
   (i) comprises under the control of an inducible promoter a nucleotide sequence encoding a phage protein which inhibits growth of said bacterial host cell wherein said phage protein which inhibits growth of said bacterial host cell is
   (a) a protein having the amino acid sequence shown in Seq Id No: 1 which inhibits bacterial host cell RNA polymerase; or
   (b) a protein having an amino acid sequence which has an identity of 80% or more to the full-length of the amino acid sequence shown in Seq Id No: 1 and which inhibits bacterial host cell RNA polymerase; and
   (ii) comprises a nucleotide sequence encoding an RNA polymerase which is heterologous for said bacterial host cell wherein said RNA polymerase, which is heterologous for said bacterial host cell is bacteriophage T3 RNA polymerase, T7 bacteriophage RNA polymerase, engineered orthogonal T7 RNA polymerase, bacteriophage SP6 RNA polymerase or bacteriophage Xp10 RNA polymerase; and
   (iii) comprises a nucleotide sequence which encodes a protein of interest under the control of a promoter recognized by said RNA polymerase, which is heterologous for said host cell,
   wherein said nucleotide sequence encoding a phage protein which inhibits growth of said bacterial host cell and said nucleotide sequence encoding said RNA polymerase, which is heterologous for said bacterial host cell are integrated into the genome of said host cell.

7. A method for the production of a protein of interest, comprising culturing the bacterial host cell of claim 1 under suitable conditions and obtaining said protein of interest.

8. The method of claim 7, wherein said culturing step includes
   (a) growing the bacterial cells to a density of at least 20 g/L cell dry mass (CDM);
   (b) inducing expression of the nucleotide sequence encoding a phage protein which inhibits growth of the host cell;
   (c) feeding bacterial cells with a constant linear feed rate that would allow an initial growth rate of 0.05 $h^{-1}$; and
   (d) further culturing said bacterial cells for at least 12 hours.

9. A method for increasing the yield of a protein of interest, comprising transforming a bacterial host which is *E. coli* and which comprises:
   (i) a nucleotide sequence encoding an RNA polymerase being heterologous for said bacterial host cell, wherein said RNA polymerase, which is heterologous for said bacterial host cell is bacteriophage T3 RNA polymerase, T7 bacteriophage RNA polymerase, engineered orthogonal T7 RNA polymerase, bacteriophage SP6 RNA polymerase or bacteriophage XP10 RNA polymerase; and
   (ii) a nucleotide sequence which encodes said protein of interest, wherein said nucleotide sequence, which encodes said protein of interest is under the control of a promoter which is recognized by said RNA polymerase being heterologous for said bacterial host cell;
   with a nucleotide sequence encoding a phage protein which inhibits growth of said bacterial host cell, wherein said nucleotide sequence encoding a phage protein which inhibits growth of said bacterial host cell is under the control of an inducible promoter,
   wherein said nucleotide sequence encoding a phage protein which inhibits growth of said bacterial host cell and sail nucleotide sequence encoding said RNA polymerase being heterologous for said bacterial host cell are integrated into the genome of sail host cell, and wherein said phage protein which inhibits growth of said bacterial host cell is (a) a protein having the amino acid sequence shown in Seq Id No: 1 which inhibits bacterial host cell RNA polymerase; or (b) a protein having an amino acid sequence which has an identity of 80% or more to the full-length of the amino acid sequence shown in Seq Id No: 1 and which inhibits bacterial host cell RNA polymerase.

10. A method for the production of a protein of interest, comprising bringing into contact under suitable conditions the preparation of claim 6 with a nucleotide sequence comprising under the control of a promoter recognized by an RNA polymerase as defined in claim 6 a nucleotide sequence which encodes a protein of interest.

11. The method of claim 9, wherein the protein of interest is toxic for cells, and adversely affects viability, cell growth and/or cell division.

12. The method of claim 9, further comprising modifying the protein of interest and/or formulating the protein of interest into a composition which includes at least one additional component.

13. The method of claim 12, wherein said protein of interest is modified with a label.

14. The bacterial host cell of claim 1, wherein said nucleotide sequence encoding said RNA polymerase which is heterologous for said bacterial host cell is under the control of a constitutive promoter.

* * * * *

SEQUENCE LISTING

<160> NUMBER OF SEQ ID NOS: 14

<210> SEQ ID NO 1
<211> LENGTH: 64
<212> TYPE: PRT
<213> ORGANISM: artificial
<220> FEATURE:
<223> OTHER INFORMATION: Gp2 phage protein

<400> SEQUENCE: 1

Met Ser Asn Val Asn Thr Gly Ser Leu Ser Val Asp Asn Lys Lys Phe
1               5                   10                  15

Trp Ala Thr Val Glu Ser Ser Glu His Ser Phe Glu Val Pro Ile Tyr
            20                  25                  30

Ala Glu Thr Leu Asp Glu Ala Leu Glu Leu Ala Glu Trp Gln Tyr Val
        35                  40                  45

Pro Ala Gly Phe Glu Val Thr Arg Val Arg Pro Cys Val Ala Pro Lys
    50                  55                  60

<210> SEQ ID NO 2
<211> LENGTH: 110
<212> TYPE: PRT
<213> ORGANISM: artificial

<220> FEATURE:
<223> OTHER INFORMATION: Nun phage protein

<400> SEQUENCE: 2

Met Val Lys Lys Thr Ile Tyr Val Asn Pro Asp Ser Gly Gln Asn Arg
1               5                   10                  15

Lys Val Ser Asp Arg Gly Leu Thr Ser Arg Asp Arg Arg Ile Ala
            20                  25                  30

Arg Trp Glu Lys Arg Ile Ala Tyr Ala Leu Lys Asn Gly Val Thr Pro
        35                  40                  45

Gly Phe Asn Ala Ile Asp Asp Gly Pro Glu Tyr Lys Ile Asn Glu Asp
    50                  55                  60

Pro Met Asp Lys Val Asp Lys Ala Leu Ala Thr Pro Phe Pro Arg Asp
65                  70                  75                  80

Val Glu Lys Ile Glu Asp Glu Lys Tyr Glu Asp Val Met His Arg Val
                85                  90                  95

Val Asn His Ala His Gln Arg Asn Pro Asn Lys Lys Trp Ser
            100                 105                 110

<210> SEQ ID NO 3
<211> LENGTH: 883
<212> TYPE: PRT
<213> ORGANISM: artificial
<220> FEATURE:
<223> OTHER INFORMATION: Gp0.7 phage protein

<400> SEQUENCE: 3

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp

```
                225                 230                 235                 240
Ser Glu Thr Ile Glu Leu Ala Pro Gly Tyr Ala Glu Ile Ala Thr
            245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
            275                 280                 285

Asn Gly Arg Arg Pro Leu Ala Leu Val Arg Thr His Ser Lys Lys Ala
            290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
            325                 330                 335

Val Ala Asn Val Ile Thr Lys Trp Lys His Cys Pro Val Glu Asp Ile
            340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Val
            370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
            405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
            485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
            610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655
```

```
Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
            755                 760                 765

Ile Asp Ala His Lys Gln Glu Ser Gly Ile Ala Pro Asn Phe Val His
            770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
            835                 840                 845

Phe Ala Asp Gln Leu His Glu Ser Gln Leu Asp Lys Met Pro Ala Leu
            850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 4
<211> LENGTH: 52
<212> TYPE: PRT
<213> ORGANISM: artificial
<220> FEATURE:
<223> OTHER INFORMATION: Gp6 phage protein

<400> SEQUENCE: 4

Met Arg Lys Ser Leu Ile Met Gly Thr Lys Glu Asp Val Ala Lys Met
1               5                   10                  15

Lys Ala Lys Arg Gln Met Asn Lys Ala Val Thr Phe Ala Glu Arg Tyr
            20                  25                  30

Ser Thr Ser Glu Pro Val Arg Arg Ile Val Thr Phe Asn His Pro Ala
        35                  40                  45

Ile Lys Gly Met
    50

<210> SEQ ID NO 5
<211> LENGTH: 71
<212> TYPE: PRT
<213> ORGANISM: artificial
<220> FEATURE:
<223> OTHER INFORMATION: Gp8 phage protein

<400> SEQUENCE: 5

Met Glu Gln Leu Asn Tyr Gly Tyr Lys Ile Lys Arg Asn Gln Val Arg
1               5                   10                  15
```

```
Gly Ser Trp Leu Phe Leu Val Tyr Gly Lys Pro Ile Tyr Glu Leu His
            20                  25                  30

Arg Gly Glu Lys Ser Lys Thr Tyr Tyr Val Thr His Ile Ala Thr Gly
            35                  40                  45

Lys Thr Pro Ala Cys Ala Gly Leu Leu Arg Asp Ala Ile Met Lys Ala
 50                  55                  60

Cys Met Leu Glu Gly Leu Leu
 65                  70

<210> SEQ ID NO 6
<211> LENGTH: 341
<212> TYPE: PRT
<213> ORGANISM: artificial
<220> FEATURE:
<223> OTHER INFORMATION: A* phage protein

<400> SEQUENCE: 6

Met Lys Ser Arg Arg Gly Phe Ala Ile Gln Arg Leu Met Asn Ala Met
 1               5                  10                  15

Arg Gln Ala His Ala Asp Gly Trp Phe Ile Val Phe Asp Thr Leu Thr
            20                  25                  30

Leu Ala Asp Asp Arg Leu Glu Ala Phe Tyr Asp Asn Pro Asn Ala Leu
            35                  40                  45

Arg Asp Tyr Phe Arg Asp Ile Gly Arg Met Val Leu Ala Ala Glu Gly
 50                  55                  60

Arg Lys Ala Asn Asp Ser His Ala Asp Cys Tyr Gln Tyr Phe Cys Val
 65                  70                  75                  80

Pro Glu Tyr Gly Thr Ala Asn Gly Arg Leu His Phe His Ala Val His
            85                  90                  95

Phe Met Arg Thr Leu Pro Thr Gly Ser Val Asp Pro Asn Phe Gly Arg
            100                 105                 110

Arg Val Arg Asn Arg Arg Gln Leu Asn Ser Leu Gln Asn Thr Trp Pro
            115                 120                 125

Tyr Gly Tyr Ser Met Pro Ile Ala Val Arg Tyr Thr Gln Asp Ala Phe
            130                 135                 140

Ser Arg Ser Gly Trp Leu Trp Pro Val Asp Ala Lys Gly Glu Pro Leu
145                 150                 155                 160

Lys Ala Thr Ser Tyr Met Ala Val Gly Phe Tyr Val Ala Lys Tyr Val
                165                 170                 175

Asn Lys Lys Ser Asp Met Asp Leu Ala Ala Lys Gly Leu Gly Ala Lys
            180                 185                 190

Glu Trp Asn Asn Ser Leu Lys Thr Lys Leu Ser Leu Pro Lys Lys
            195                 200                 205

Leu Phe Arg Ile Arg Met Ser Arg Asn Phe Gly Met Lys Met Leu Thr
            210                 215                 220

Met Thr Asn Leu Ser Thr Glu Cys Leu Ile Gln Leu Thr Lys Leu Gly
225                 230                 235                 240

Tyr Asp Ala Thr Pro Phe Asn Gln Ile Leu Lys Gln Asn Ala Lys Arg
                245                 250                 255

Glu Met Arg Leu Arg Leu Gly Lys Val Thr Val Ala Asp Val Leu Ala
            260                 265                 270

Ala Gln Pro Val Thr Thr Asn Leu Leu Lys Phe Met Arg Ala Ser Ile
            275                 280                 285

Lys Met Ile Gly Val Ser Asn Leu Gln Ser Phe Ile Ala Ser Met Thr
            290                 295                 300
```

```
Gln Lys Leu Thr Leu Ser Asp Ile Ser Asp Glu Ser Lys Asn Tyr Leu
305                 310                 315                 320

Asp Lys Ala Gly Ile Thr Thr Ala Cys Leu Arg Ile Lys Ser Lys Trp
            325                 330                 335

Thr Ala Gly Gly Lys
            340

<210> SEQ ID NO 7
<211> LENGTH: 69
<212> TYPE: PRT
<213> ORGANISM: artificial
<220> FEATURE:
<223> OTHER INFORMATION: Bacillus subtilis YkzG (Epsilon-Subunit)

<400> SEQUENCE: 7

Met Ile Tyr Lys Val Phe Tyr Gln Glu Lys Ala Asp Glu Val Pro Val
1               5                   10                  15

Arg Glu Lys Thr Asp Ser Leu Tyr Ile Glu Gly Val Ser Glu Arg Asp
                20                  25                  30

Val Arg Thr Lys Leu Lys Glu Lys Lys Phe Asn Ile Glu Phe Ile Thr
            35                  40                  45

Pro Val Asp Gly Ala Phe Leu Glu Tyr Glu Gln Gln Ser Glu Asn Phe
    50                  55                  60

Lys Val Leu Glu Leu
65

<210> SEQ ID NO 8
<211> LENGTH: 350
<212> TYPE: PRT
<213> ORGANISM: artificial
<220> FEATURE:
<223> OTHER INFORMATION: Bacillus phage SPO1 GP40

<400> SEQUENCE: 8

Met His Ile Tyr Thr Tyr Trp Gly Leu Lys Tyr Val Pro Ser Asn Ser
1               5                   10                  15

Thr Met Val Ala Lys Glu Gly Asp Leu Ile Leu Leu Gly Asn Glu Val
                20                  25                  30

His Lys Val Val Lys Val Leu His Arg Phe Arg Asn Ile Thr Asp Leu
            35                  40                  45

Gln Ile Thr Asn Trp Lys Gly Thr Glu Thr Arg Tyr Asn Leu His Val
    50                  55                  60

Thr Glu Tyr Lys Val Leu Val Pro Tyr Asp Thr His Lys Glu Glu Asn
65                  70                  75                  80

Glu Ala Met Ser Asp Ser Leu Ile Thr His Asn Gly Lys Asp Tyr Val
                85                  90                  95

Leu Cys Lys Ile Pro Ala Arg Val Gly Asp Leu Ile Arg Thr Glu Asp
            100                 105                 110

Lys Arg Val Trp Glu Val Leu Gln Lys Ser Lys Asp Gly Leu Val Leu
    115                 120                 125

Tyr Asn Glu Glu Lys Gly Glu Gln Arg Ser Ala Val Tyr Ser Glu Ile
130                 135                 140

Gly Pro Tyr His Val Leu Val Pro Arg Asp Thr Asp Thr His Thr Pro
145                 150                 155                 160

Thr Arg Glu Glu Leu Ala Ala Val Ile Met Asn Lys Ala Phe Thr Arg
                165                 170                 175

Thr Glu Thr Gln Asp Ser Gln Glu Asp Thr Gly Thr His Lys Gly Leu
```

```
                180                 185                 190
Gly Leu Thr Gly Thr Asp Leu Tyr His Ser Leu Arg Asp Leu Asp Ala
            195                 200                 205
Lys Val Gln Ser Gly Tyr Tyr Thr Ala Thr Glu Asn Glu Glu Asp Val
            210                 215                 220
Lys Ser Glu Ile Glu Ala Thr Lys Lys His Met Lys Ala Val Lys Glu
225                 230                 235                 240
Ser Gly Lys Thr Val Asn Asp Tyr Arg Lys Glu Glu Asn Thr Lys Arg
            245                 250                 255
Cys Lys Leu Lys Ala Leu Thr Asn Lys Phe Asn Arg Leu Phe Leu Lys
            260                 265                 270
Ser Val Ile Asp Thr Asp Ser Leu Gln Val Gly Lys Ala Tyr Leu Ile
            275                 280                 285
Gly Gly Arg Asp Met Lys Asn Val His Gly Leu Tyr Thr Gly Thr Thr
            290                 295                 300
Phe Asp Gln Gln His Ala Asn Phe Leu Ile Val Glu Thr Asp Arg Met
305                 310                 315                 320
His Arg Thr Leu Thr Val Ser Ala Glu Gln Leu Phe Ala Glu Glu Arg
            325                 330                 335
His Ile Val Asp Ile Glu Lys Arg Val Glu Gln Thr Glu Asp
            340                 345                 350

<210> SEQ ID NO 9
<211> LENGTH: 202
<212> TYPE: PRT
<213> ORGANISM: artificial
<220> FEATURE:
<223> OTHER INFORMATION: Staphylococcus phage G1 GP67

<400> SEQUENCE: 9

Met Thr Asn Ser Lys Lys Lys Gly Asp Thr Phe Glu Arg Lys Ile Ala
1               5                   10                  15
Lys Glu Leu Thr Ala Trp Trp Gly Tyr Gln Phe Asn Arg Ser Pro Gln
            20                  25                  30
Ser Gly Gly Ala Ser Trp Gly Lys Asp Asn Asn Ala Val Gly Asp Ile
        35                  40                  45
Val Val Pro Gln Glu Ala Asn Phe Pro Leu Val Val Glu Cys Lys His
    50                  55                  60
Arg Glu Glu Trp Thr Ile Asp Asn Val Leu Leu Asn Asn Arg Glu Pro
65                  70                  75                  80
His Thr Trp Trp Glu Gln Val Ile Asn Asp Ser Ser Lys Val Asn Lys
                85                  90                  95
Thr Pro Cys Leu Ile Phe Thr Arg Asn Arg Ala Gln Ser Tyr Val Ala
            100                 105                 110
Leu Pro Tyr Asp Glu Lys Val Tyr Glu Asp Leu Arg Asn Asn Glu Tyr
        115                 120                 125
Pro Val Met Arg Thr Asp Phe Ile Ile Asp Asn Ile Arg Lys Asp Lys
    130                 135                 140
Phe Phe Tyr Asp Val Leu Ile Thr Thr Met Asn Gly Leu Thr Ser Phe
145                 150                 155                 160
Thr Pro Ser Tyr Ile Ile Ser Cys Tyr Asp Lys Lys Asp Ile Lys Pro
                165                 170                 175
Tyr Lys Lys Val Glu Ser Asn Leu Ser Glu Val Ser Lys His Glu Asp
            180                 185                 190
Glu Leu Ile Asn Asp Leu Leu Ser Asp Ile
```

```
                195                 200

<210> SEQ ID NO 10
<211> LENGTH: 141
<212> TYPE: PRT
<213> ORGANISM: artificial
<220> FEATURE:
<223> OTHER INFORMATION: Thermus thermophilus phage P23-45 GP39

<400> SEQUENCE: 10

Met Val Glu Gly Phe Val Glu Pro Tyr Ile Arg Leu Phe Glu Ala Ile
1               5                   10                  15

Pro Asp Ala Glu Thr Glu Leu Ala Thr Phe Tyr Asp Ala Asp Leu Asp
            20                  25                  30

Thr Leu Pro Pro Arg Met Phe Leu Pro Ser Gly Asp Leu Tyr Thr Pro
        35                  40                  45

Pro Gly Pro Val Arg Leu Glu Glu Ile Lys Arg Lys Arg Val Arg
    50                  55                  60

Leu Val Lys Val Ser Ile Tyr Arg Phe Glu His Val Gly Leu Gly Leu
65                  70                  75                  80

Ala Ala Arg Pro Tyr Ala Tyr Ala Tyr Ala Trp Gln Gly Asp Asn Gly
                85                  90                  95

Ile Leu His Leu Tyr His Ala Pro Val Val Leu Glu Asp Val Pro Glu
            100                 105                 110

Val Leu Glu Leu Asp Glu Val Thr Tyr Asn Glu Ser Tyr Val Arg Leu
        115                 120                 125

Met Arg Ala Met Gly His Val Asp Ala Phe Ile Asp Leu
    130                 135                 140

<210> SEQ ID NO 11
<211> LENGTH: 82
<212> TYPE: PRT
<213> ORGANISM: artificial
<220> FEATURE:
<223> OTHER INFORMATION: Enterobacteria phage PhiEco32 GP79

<400> SEQUENCE: 11

Met Asp Met Phe Ser Leu Glu Asp Leu Val Gln Asn Gly Met Met Glu
1               5                   10                  15

Gln Lys Glu Pro Leu Ile Val Gly Ser Arg Lys Glu Leu Arg Lys Leu
            20                  25                  30

Cys Glu Glu Trp Gly Ile Thr Asn Gln Arg Met Ile Gly Asn Gln Phe
        35                  40                  45

Ser Ala Ile Val Thr Phe Leu Lys Arg Gly Asp Lys Tyr Ser Met Glu
    50                  55                  60

Cys Val Glu Arg Ile Ile Thr Glu Ala Gln Gln Asp Lys Gly Val Thr
65                  70                  75                  80

Tyr Leu

<210> SEQ ID NO 12
<211> LENGTH: 73
<212> TYPE: PRT
<213> ORGANISM: artificial
<220> FEATURE:
<223> OTHER INFORMATION: Xanthomonas oryzae bacteriophage Xp10 P7

<400> SEQUENCE: 12

Met Asn Glu Phe Thr Gln Ile Ser Gly Tyr Val Asn Ala Phe Gly Ser
1               5                   10                  15
```

Gln Arg Gly Ser Val Leu Thr Val Lys Val Glu Asn Asp Glu Gly Trp
            20                  25                  30

Thr Leu Val Glu Glu Asp Phe Asp Arg Ala Asp Tyr Gly Ser Asp Pro
        35                  40                  45

Glu Phe Val Ala Glu Val Ser Ser Tyr Leu Lys Arg Asn Gly Gly Ile
50                  55                  60

Lys Asp Leu Thr Lys Val Leu Thr Arg
65                  70

<210> SEQ ID NO 13
<211> LENGTH: 167
<212> TYPE: PRT
<213> ORGANISM: artificial
<220> FEATURE:
<223> OTHER INFORMATION: Enterobacteria phage T4 Alc

<400> SEQUENCE: 13

Met Asp Leu Gln Leu Ile Thr Thr Glu Met Val Val Glu Ala Tyr Gly
1               5                   10                  15

Asp Thr Thr Asp Gly Ile Ser Val Phe Lys Gly Asn Arg Arg Val Gly
            20                  25                  30

Tyr Ile Thr Gly Leu Lys Lys Asp Leu Ala Lys Gln Val Lys Arg Lys
        35                  40                  45

Thr Thr Ile Lys Glu Tyr Arg Asn Arg Leu Glu Gln Ala Arg Asp
50                  55                  60

Met Leu Pro Asp Ala Val Glu Glu Met Lys Val Phe Leu Glu Asn Gln
65                  70                  75                  80

Leu Ala Lys Tyr Asp Cys Glu Val Phe Ile Asn Gln Thr Gln Pro Asn
                85                  90                  95

Val His Ile Asn Ser Cys Lys Cys Tyr Ile Ile Val Asn Pro Leu Thr
            100                 105                 110

Gly Lys His Arg Leu Gly Ile Ser Asn Pro Asn Arg Ser Ala Ser Asp
        115                 120                 125

Met Ala Glu Asp Val Glu Ala Cys Phe Lys Ile Ser Lys Ser Pro Ala
130                 135                 140

Glu His His Ile Leu Ile Asn Gly Leu Ser Gln Asp Asp Ile Val Glu
145                 150                 155                 160

Val Ile Lys Thr Leu Cys Met
                165

<210> SEQ ID NO 14
<211> LENGTH: 90
<212> TYPE: PRT
<213> ORGANISM: artificial
<220> FEATURE:
<223> OTHER INFORMATION: Enterobacteria phage T4 Asia

<400> SEQUENCE: 14

Met Asn Lys Asn Ile Asp Thr Val Arg Glu Ile Ile Thr Val Ala Ser
1               5                   10                  15

Ile Leu Ile Lys Phe Ser Arg Glu Asp Ile Val Glu Asn Arg Ala Asn
            20                  25                  30

Phe Ile Ala Phe Leu Asn Glu Ile Gly Val Thr His Glu Gly Arg Lys
        35                  40                  45

Leu Asn Gln Asn Ser Phe Arg Lys Ile Val Ser Glu Leu Thr Gln Glu
50                  55                  60

```
Asp Lys Lys Thr Leu Ile Asp Glu Phe Asn Glu Gly Phe Glu Gly Val
65                  70                  75                  80

Tyr Arg Tyr Leu Glu Met Tyr Thr Asn Lys
                85                  90
```